United States Patent
Johnson et al.

(10) Patent No.: US 6,355,806 B1
(45) Date of Patent: Mar. 12, 2002

(54) ACETYLENES DISUBSTITUTED WITH A 5 ALKYL, ARYL OR HETEROARYL SUBSTITUTED DIHYDRONAPHTHYL GROUP AND WITH AN ARYL OR HETEROARYL GROUP HAVING RETINOID-LIKE WITH AN ARYL OR HETEROARYL GROUP HAVING RETINOID-LIKE BIOLOGICAL ACTIVITY

(75) Inventors: Alan T. Johnson, Rancho Santa Margarita; Min Teng, Aliso Viejo; Vidyasagar Vuligonda, Irvine; Richard L. Beard, Newport Beach; Samuel J. Gillett, Albany; Tien T. Duong, Irvine; Roshantha A. Chandraratna, Mission Viejo, all of CA (US)

(73) Assignee: Allergen Sales, Inc., Irvine, CA (US)

( * ) Notice: Subject to any disclaimer, the term of this patent is extended or adjusted under 35 U.S.C. 154(b) by 0 days.

(21) Appl. No.: 09/398,613

(22) Filed: Sep. 16, 1999

Related U.S. Application Data

(62) Division of application No. 09/132,435, filed on Aug. 11, 1998, which is a division of application No. 08/854,297, filed on May 12, 1997, now Pat. No. 5,808,083, which is a division of application No. 08/366,193, filed on Dec. 29, 1994, now Pat. No. 5,648,514.

(51) Int. Cl.[7] .......................................... C07D 211/70
(52) U.S. Cl. ...................... 546/348; 548/202; 548/215; 548/333.5; 549/80; 549/506; 544/239; 544/335; 544/406
(58) Field of Search ...................... 546/348; 548/202, 548/215, 333.5; 549/80, 506; 544/239, 406, 335

(56) References Cited

U.S. PATENT DOCUMENTS

| | | |
|---|---|---|
| 4,096,341 A | 6/1978 | Frazer |
| 4,326,055 A | 4/1982 | Loeliger |
| 4,391,731 A | 7/1983 | Boller et al. ........... 252/299.26 |
| 4,485,252 A | 11/1984 | Fuchs et al. ................... 560/8 |
| 4,539,154 A | 9/1985 | Krebs ........................ 260/410 |
| 4,695,649 A | 9/1987 | Magami et al. |
| 4,723,028 A | 2/1988 | Shudo |
| 4,739,098 A | 4/1988 | Chandraratna |
| 4,740,519 A | 4/1988 | Shroot et al. |
| 4,810,804 A | 3/1989 | Chandraratna |
| 4,826,969 A | 5/1989 | Maignan et al. |
| 4,826,984 A | 5/1989 | Berlin et al. ................. 546/134 |
| 4,833,240 A | 5/1989 | Maignan et al. ........... 536/55.2 |
| 4,855,320 A | 8/1989 | Chatterjee et al. |
| 4,895,868 A | 1/1990 | Chandraratna |
| 4,923,884 A | 5/1990 | Chandraratna ............. 514/354 |
| 4,927,947 A | 5/1990 | Chandraratna ............. 549/484 |
| 4,980,369 A | 12/1990 | Chandraratna |
| 4,992,468 A | 2/1991 | Chandraratna |
| 5,006,550 A | 4/1991 | Chandraratna |
| 5,013,744 A | 5/1991 | Chandraratna |
| 5,015,658 A | 5/1991 | Chandraratna |
| 5,023,341 A | 6/1991 | Chandraratna |
| 5,037,825 A | 8/1991 | Klaus et al. ............. 514/233.8 |
| 5,045,551 A | 9/1991 | Chandraratna |
| 5,053,523 A | 10/1991 | Chandraratna |
| 5,068,252 A | 11/1991 | Chandraratna |
| 5,089,509 A | 2/1992 | Chandraratna |
| 5,130,335 A | 7/1992 | Chandraratna |
| 5,134,159 A | 7/1992 | Chandraratna |

(List continued on next page.)

FOREIGN PATENT DOCUMENTS

| | | | |
|---|---|---|---|
| DE | 3316932 | 11/1983 | ........... C07C/63/66 |
| DE | 3524199 | 1/1986 | ........... C07C/63/66 |
| DE | 3602473 | 7/1987 | ......... C07C/43/215 |
| DE | 3708060 | 9/1987 | ......... C07D/311/04 |
| DE | 3715955 | 11/1987 | ........... C07C/15/58 |
| EP | 0098591 | 1/1984 | ......... C07D/333/54 |
| EP | 0130795 | 1/1985 | ......... C07D/311/58 |
| EP | 170105 A | 2/1986 | |

(List continued on next page.)

OTHER PUBLICATIONS

Gruapner, et al., "6'–Substituted Naphthalene–2–Carboxylic Acid Analogs, A New Class of Retinoic Acid Receptor Subtype–Specific Ligands," *Biochemical and Biophysical Communications*, vol. 179, No. 3 (Sep. 30, 1991), pp. 1554–1561.

Moore, et al., "Retinoic Acid and Interferon in Human Cancer: Mechanistic and Clinical Studies," *Seminars in Hematology*, 31/4, Suppl 5 (Oct. 1994), pp. 31–37.

Jones, et al., "A dose–response study of 13–cis–retinoic acid in acne vulgaris", *British Journal of Dermatology*, (1983) 108, 333–343.

Fekrat, et al., "The Effect of Oral 13–cis–retinoic Acid on Retinal Redetachment after Surgical Repair in Eyes with Proliferative Viteoretinopathy", *Ophthalmology*, vol. 102, No. 3 (Mar. 1995), pp. 412–418.

(List continued on next page.)

*Primary Examiner*—Samuel Barts
(74) *Attorney, Agent, or Firm*—Gabor L. Szekeres; Robert J. Baran; Martin A. Voet

(57) ABSTRACT

Compounds of the formula

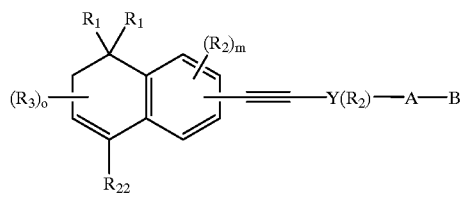

wherein the symbols have the meaning described in the specification, have retinoid-like biological activity.

13 Claims, No Drawings

U.S. PATENT DOCUMENTS

| | | | |
|---|---|---|---|
| 5,162,546 A | 11/1992 | Chandraratna | 549/23 |
| 5,175,185 A | 12/1992 | Chandraratna | 514/445 |
| 5,183,827 A | 2/1993 | Chandraratna | 514/444 |
| 5,202,471 A | 4/1993 | Chandraratna | 562/473 |
| 5,231,113 A | 7/1993 | Chandraratna | 514/510 |
| 5,234,926 A | 8/1993 | Chandraratna | 514/253 |
| 5,248,777 A | 9/1993 | Chandraratna | 546/165 |
| 5,264,456 A | 11/1993 | Chandraratna | 514/461 |
| 5,264,578 A | 11/1993 | Chandraratna | 546/269 |
| 5,272,156 A | 12/1993 | Chandraratna | 514/314 |
| 5,278,318 A | 1/1994 | Chandraratna | 549/23 |
| 5,324,744 A | 6/1994 | Chandraratna | 514/456 |
| 5,324,840 A | 6/1994 | Chandraratna | 546/318 |
| 5,326,898 A | 7/1994 | Chandraratna | 560/17 |
| 5,344,959 A | 9/1994 | Chandraratna | 560/100 |
| 5,346,895 A | 9/1994 | Chandraratna | 514/247 |
| 5,346,915 A | 9/1994 | Chandraratna | 514/432 |
| 5,348,972 A | 9/1994 | Chandraratna | 514/432 |
| 5,348,975 A | 9/1994 | Chandraratna | 514/456 |
| 5,349,105 A | 9/1994 | Chandraratna | 564/163 |
| 5,354,752 A | 10/1994 | Chandraratna | 514/252 |
| 5,354,776 A | 10/1994 | Chandratatna | 514/461 |
| 5,380,877 A | 1/1995 | Chandraratna | 549/60 |
| 5,391,753 A | 2/1995 | Chandraratna | 546/323 |
| 5,399,561 A | 3/1995 | Chandraratna | 514/252 |
| 5,399,586 A | 3/1995 | Davies et al. | 514/448 |
| 5,407,937 A | 4/1995 | Chandraratna | 514/256 |
| 5,414,007 A | 5/1995 | Chandraratna | 514/365 |
| 5,420,145 A | 5/1995 | Shudo | 514/352 |
| 5,426,118 A | 6/1995 | Chandraratna | 514/337 |
| 5,434,173 A | 7/1995 | Chandraratna | 514/354 |
| 5,451,605 A | 9/1995 | Chandraratna et al. | 514/475 |
| 5,455,265 A | 10/1995 | Chandraratna | 514/448 |
| 5,466,861 A | 11/1995 | Dawson et al. | 560/100 |
| 5,468,879 A | 11/1995 | Chandraratna | 549/23 |
| 5,470,999 A | 11/1995 | Chandraratna | 560/100 |
| 5,475,022 A | 12/1995 | Chandraratna | 514/448 |
| 5,475,113 A | 12/1995 | Chandraratna | 548/203 |
| 5,489,584 A | 2/1996 | Vuligonda et al. | 514/188 |
| 5,498,755 A | 3/1996 | Chandraratna et al. | 564/272 |
| 5,498,795 A | 3/1996 | Song et al. | 562/474 |
| 5,514,825 A | 5/1996 | Vuligonda et al. | 558/462 |
| 5,516,904 A | 5/1996 | Chandraratna | 514/269 |
| 5,523,457 A | 6/1996 | Starrett, Jr. et al. | 560/24 |
| 5,534,516 A | 7/1996 | Chandraratna | 514/253 |
| 5,534,641 A | 7/1996 | Song et al. | 549/416 |
| 5,543,534 A | 8/1996 | Vuligonda et al. | 549/421 |
| 5,556,996 A | 9/1996 | Beard et al. | 549/407 |
| 5,559,248 A | 9/1996 | Starrett, Jr. et al. | 549/79 |
| 5,563,292 A | 10/1996 | Sheh et al. | 560/255 |
| 5,591,858 A | 1/1997 | Vuligonda et al. | 546/322 |
| 5,599,819 A | 2/1997 | Chandraratna | 514/314 |
| 5,599,967 A | 2/1997 | Vuligonda et al. | 560/48 |
| 5,602,130 A | 2/1997 | Chandraratna | 514/247 |
| 5,602,135 A | 2/1997 | Chandraratna | 514/252 |
| 5,605,915 A | 2/1997 | Vuligond et al. | 514/356 |
| 5,616,597 A | 4/1997 | Chandraratna | 514/365 |
| 5,616,712 A | 4/1997 | Teng et al. | 546/158 |
| 5,618,836 A | 4/1997 | Chandraratna et al. | 514/444 |
| 5,618,931 A | 4/1997 | Beard et al. | 544/224 |
| 5,618,943 A | 4/1997 | Vuligonda et al. | 546/342 |
| 5,648,503 A | 7/1997 | Vuligonda et al. | 549/13 |
| 5,648,514 A | 7/1997 | Johnson et al. | 560/102 |
| 5,654,469 A | 8/1997 | Vuligonda et al. | 560/56 |
| 5,663,347 A | 9/1997 | Chandraratna | 546/152 |
| 5,663,357 A | 9/1997 | Teng et al. | 546/323 |
| 5,663,367 A | 9/1997 | Vuligonda et al. | 549/4 |
| 5,672,710 A | 9/1997 | Beard et al. | 548/188 |
| 5,675,024 A | 10/1997 | Teng et al. | 549/405 |
| 5,675,033 A | 10/1997 | Vuligonda et al. | 560/100 |
| 5,677,320 A | 10/1997 | Chandraratna | 514/365 |
| 5,677,323 A | 10/1997 | Chandraratna | 514/374 |
| 5,677,451 A | 10/1997 | Chandraratna | 544/238 |
| 5,808,083 A | 9/1998 | Johnson et al. | 546/348 |

FOREIGN PATENT DOCUMENTS

| | | | |
|---|---|---|---|
| EP | 0176032 | 4/1986 | C07C/65/38 |
| EP | 0176033 | 4/1986 | C07D/261/18 |
| EP | 0253302 | 1/1988 | C07D/213/16 |
| EP | 0272921 | 6/1988 | C07D/213/80 |
| EP | 0284261 | 9/1988 | C07D/213/80 |
| EP | 0284288 | 9/1988 | C07D/401/04 |
| EP | 0286364 | 10/1988 | C07C/103/78 |
| EP | 0303186 | 2/1989 | |
| EP | 0303915 | 2/1989 | A61K/31/255 |
| EP | 176034 A | 4/1989 | C07C/63/66 |
| EP | 0315071 | 5/1989 | C07C/63/66 |
| EP | 0350846 | 7/1989 | C07D/311/85 |
| EP | 0412387 | 2/1991 | C07C/317/14 |
| EP | 0478787 | 10/1991 | C07C/233/65 |
| EP | 0514269 | 11/1992 | C07C/257/08 |
| EP | 0617020 | 9/1994 | C07D/213/82 |
| EP | 0619116 | 10/1994 | A61K/31/19 |
| EP | 0661259 | 5/1995 | C07C/233/81 |
| EP | 0661258 | 7/1995 | C07D/65/19 |
| EP | 0661261 | 7/1995 | C07C/235/84 |
| EP | 0718285 | 8/1996 | C07C/403/20 |
| GB | 2190378 | 11/1987 | C07C/39/21 |
| WO | 85/00806 | 2/1985 | A61K/31/00 |
| WO | 85/04652 | 10/1985 | A61K/31/19 |
| WO | 91/16051 | 10/1991 | A61K/31/44 |
| WO | 92/06948 | 4/1992 | C07C/69/86 |
| WO | 93/03713 | 3/1993 | A61K/31/07 |
| WO | 93/11755 | 6/1993 | A61K/31/07 |
| WO | 93/21146 | 10/1993 | C07C/69/76 |
| WO | 94/14777 | 7/1994 | C07D/231/54 |
| WO | 95/04036 | 2/1995 | C07C/403/20 |
| WO | 96/05165 | 2/1996 | C07C/57/50 |

OTHER PUBLICATIONS

Nagpal, et al., "Separation of Transactivation and AP1 Antagonism Functions of Retinoic Acid Receptor α", *The Journal of Biological Chemistry*, 270/2(1995):923–927.

Allegretto, et al., "Transactivation Properties of Retinoic Acid and Retinoid X Receptors in Mammalian Cells and Yeast", *The Journal of Biological Chemistry*, vol. 268, No. 35 (Dec. 15, 1993), pp. 26625–26633.

Biochemical and Biophysical Research Communications, vol. 155 No. 1, 1988, pp. 503–508.

Chemical Abstracts. vol. 121, No. 9, 1994.

Database WPI, Section CH, Week 9416, Derwent Publications Ltd. London, GB; Class B05, AN 94–128759 and JP 6078266A, see English language abstract in Derwent.

Journal of Medicinal Chemistry, vol. 38, No. 16, Aug. 4, 1995, pp. 3163–3173.

Liu S. S. et al. "Systemic Pharmacokinetics of Acetylenic Retinoids in Rats", *Drug Metabolism and Disposition*, (1990) 18/6: 1071–1077.

Chemical Abstracts, vol. 122, No. 13, Mar. 27, 1995 abstract No. 151372m, (S. Kaku et al.).

Chemical Abstracts, vol. 117, No. 13, Sep. 28, 1992 abstract No. 124091j, (S. Sun et al.).

European Journal of Biochemistry, vol. 212, No. 1, 1993, Berlin, pp. 13–26, XP000618300 (S. Keidel et al.).

Journal of Medicinal Chemistry, vol. 39, No. 16, Aug. 2, 1996, pp. 3035–3038, Min Teng et al.

Journal of Medicinal Chemistry, vol. 37, No. 10, May 13, 1994, pp. 1508–1517, Laurence Eyrolles.

"Di– and Tri–methoxystyryl Derivatives of Heterocyclic Nitrogen Compounds" by Bahner,C. T. et al. *Arzneim–Forsch./Drug Res*, (1981)31 (I), Nr. 3.

"Retinobenzoic acids. 3. Structure–Activity Relationships of Retinoidal Azobenzene–4–Carboxylic Acids and Stilbene–4–Carboxylic Acids" by H. Kagechika et al., *Journal of Medicinal Chemistry*, (1989), 32:1098–1108.

Eyrolles, L. et al. "Retinoid Antagonists: Molecular Design Based on the Ligand Superfamily Concept" *Med. Chem. Res.*, (1992) 2:361–367.

"Synthesis and Evaluation of Stilbene and Dihydrostilbene Derivateives as Potential Anticancer Agents That Inhibit Tubulin Polymerization" by Cushman, Mark et al. *J. Med. Chem.*, (1991), 34:2579–2588.

"Synthesis and Evaluatinof New Pretoein Tyrosine Kinase Inhibitors. Part 1. Pyridine Containing Stilbenes and Amides" by Cushman, Mark et al. *Bioorganic & Medicinal Chemistry Letters*, (1991) 1/4:211–214.

"Effects of 13–Cis–Retinoic Acid, All Trans–Retinoic Acid, and Acitretin on the Proliferation, Lipid Synthesis and Keratin Expression of Cultured Human Sebocytes in Vitro" C.C. Zouboulis, *The Journal of Investigative Dermatology*, (1991) 96/5:792–797.

"Organ Maintenance of Human Sebaceous Glands: in Vitro Effects of 13–Cis Retinoic Acid and Testosterone", John Ridden, et al., *Journal of Cell Science* (1990) 95:125–136.

"Characterization of Human Sebaceous Cells in Vitro", Thomas I. Doran, et al. *The Journal of Investigative Dermatology*, (1991) 96/3.

A Dopamine Receptor Model and Its Application in the Design of a New Class of Rigid Pyrrolo[2,3–g]isoquinoline Antipsychotics, Gary L. Olson et al. *American Chemical Societe*, (1981) 24/9:1026–1031.

6.2.3 Conformational Restriction, Williams, et al., *Drug Discovery and Development*, The Humana Press, (1987) pp. 54–55.

V. Retinoid Structrue–Biological Activity Relationships, Chemistry and Biology of Synthetic Retinoids, (1990) pp. 324–356.

Davis et al. *J. Organometallic Chem* (1990) 387:381–390.

"A Convenient Synthesis of Ethynylarenes and Diethynylarenes" by S. Takahashi et al. *Synthesis* (1980) pp. 627–630.

Shudo et al. in *Chem. Phar. Bull.*, (1985) 33:404–407.

Kagechika et al. in *J. Med. Chem.*, (1988) 31:2182–2192.

Chemistry and Biology of Synthetic Retinoids by Marcia I. Dawson and William H. Okamura, published by CRC Press Inc., 1990, pp. 334–335, 354.

Synthesis of 2,2'–Diacyl–1,1'–Biaryls. Regiocontrolled Protection of . . . by Mervic, et al, *J. Org. Chem.*,(1980) No. 45, pp. 4720–4725.

A General Synthesis of Terminal and Internal Arylalkynes by the Palladium–Catalyzed Reaction of Alkynylzinc Reagents with Aryl Halides by Anthony O. King and Ei–i-chi, *J. Org. Chem.*, (1978) 43/2: p. 358.

Conversion of Methyl Ketones into Terminal Acetylenes and (E)–Tri–substituted Olefins of Terpenoid Orgin by Ei–ichi, et al., *J. Org. Chem.*, (1980) 45/12: p. 2526.

Sporn et al. in *J. Amer. Acad. Derm. .*, (1986) 15:756–764.

ACETYLENES DISUBSTITUTED WITH A 5 ALKYL, ARYL OR HETEROARYL SUBSTITUTED DIHYDRONAPHTHYL GROUP AND WITH AN ARYL OR HETEROARYL GROUP HAVING RETINOID-LIKE WITH AN ARYL OR HETEROARYL GROUP HAVING RETINOID-LIKE BIOLOGICAL ACTIVITY

This application is a divisional of pending application Ser. No. 09/132,435, filed Aug. 11, 1998, which is a divisional of application Ser. No. 08/854,927 filed May 12, 1997, now issued as U.S. Pat. No. 5,808,083 which is a divisional of application Ser. No. 08/366,193, filed Dec. 29, 1994, now U.S. Pat. No. 5,648,514.

FIELD OF THE INVENTION

The present invention relates to novel compounds having retinoid-like activity. More specifically, the present invention relates to compounds having an acetylene portion which is substituted with a 5 substituted dihydronaphthyl and by a substituted aryl or substituted heteroaryl group having an acid function. The acid function may also be converted to an alcohol, aldehyde or ketone or derivatives thereof, or may be reduced to —$CH_3$.

BACKGROUND ART

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

U.S. Pat. No. 4,740,519 (Shroot et al.), U.S. Pat. No. 4,826,969 (Maignan et al.), U.S. Pat. No. 4,326,055 (Loeliger et al.), U.S. Pat. No. 5,130,335 (Chandraratna et al.), U.S. Pat. No. 5,037,825 (Klaus et al.), U.S. Pat. No. 5,231,113 (Chandraratna et al.), U.S. Pat. No. 5,324,840 (Chandraratna), Published European Patent Application Nos. 0 176 034 A (Wuest et al.), 0 350 846 A (Klaus et al.), 0 176 032 A (Frickel et al.), 0 176 033 A (Frickel et al.), 0 253 302 A (Klaus et al.), 0 303 915 A (Bryce et al.), UK Patent Application GB 2190378 A (Klaus et al.), German Patent Application Nos. DE 3715955 Al (Klaus et al.), DE 3602473 Al (Wuest et al., and the articles J. Amer. Acad. Derm. 15: 756–764 (1986) (Sporn et al.), Chem. Pharm. Bull. 33: 404–407 (1985) (Shudo et al.), J. Med Chem. 1988 31, 2182–2192 (Kagechika et al.), Chemistry and Biology of Synthetic Retinoids CRC Press Inc. 1990 p 334–335, 354 (Dawson et al.), describe or relate to compounds which include a tetrahydronaphthyl moiety and have retinoid-like or related biological activity. U.S. Pat. No. 4,391,731 (Boller et al.) describes tetrahydronaphthalene derivatives which are useful in liquid crystal compositions. Several co-pending applications and recently issued patents which are assigned to the assignee of the present application, are directed to further compounds having retinoid-like activity.

SUMMARY OF THE INVENTION

The present invention covers compounds of Formula

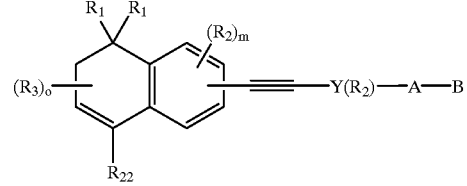

Formula 7 wherein $R_1$ is hydrogen or alkyl of 1 to 10 carbons;

$R_2$ and $R_3$ are hydrogen, or alkyl of 1 to 6 carbons and the substituted ethynyl group occupies either the 2 or the 3 position of the dihydronaphthalene nucleus;

m is an integer having the value of 0–3;

o is an is an integer having the value 0–3;

Y is a phenyl group, or heteroaryl selected from a group consisting of pyridyl, thienyl, furyl, pyridazinyl, pyrimidinyl, pyrazinyl, thiazolyl, oxazolyl, and imidazolyl, said groups being optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or trimethylsilylalkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, and R$_{22}$ is hydrogen, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, C$_1$–C$_{10}$-alkylphenyl, naphthyl, C$_1$–C$_{10}$-alkylnaphthyl, phenyl-C$_1$–C$_{10}$alkyl, naphthyl-C$_1$–C$_{10}$alkyl, C$_1$–C$_{10}$-alkenylphenyl having 1 to 3 double bonds, C$_1$–C$_{10}$-alkynylphenyl having 1 to 3 triple bonds, phenyl-C$_1$–C$_{10}$alkenyl having 1 to 3 double bonds, phenyl-C$_1$–C$_{10}$alkynyl having 1 to 3 triple bonds, hydroxy alkyl of 1 to 10 carbons, hydroxyalkynyl having 2 to 10 carbons and 1 to 3 triple bonds, acyloxyalkyl of 1 to 10 carbons or acyloxyalkynyl of 2 to 10 carbons and 1 to 3 triple bonds, where the acyl group is represented by COR$_{14}$, CN, CON(R$_1$)$_2$, (CH$_2$)$_p$CO$_2$R$_8$ where p is an integer between 0 to 10, or R$_{22}$is aminoalkyl or thio-alkyl of 1 to 10 carbons, or a 5 or 6 membered heteroaryl group optionally substituted with a C$_1$ to C$_{10}$ alkyl group and having 1 to 3 heteroatoms, said heteroatoms being selected from a group consisting of O, S, and N, or R$_{22}$ is represented by (CH$_2$)$_p$XR$_1$ or by (CH$_2$)$_p$NR$_{12}$; where X is O or S, the R$_{14}$ group is hydrogen, alkyl of 1 to 10 carbons, alkenyl of 2 to 10 carbons and having 1 to 3 double bond, alkynyl having 2 to 10 carbons and 1 to 3 triple bonds, carbocyclic aryl selected from the group consisting of phenyl, C$_1$–C$_{10}$-alkylphenyl, naphthyl, C$_1$–C$_{10}$-alkylnaphthyl, phenyl-C$_1$–C$_{10}$alkyl, or naphthyl-C$_1$–C$_{10}$alkyl.

In a second aspect, this invention relates to the use of the compounds of Formula 7 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In. addition, the present compounds can be used as agents to treat diseases of the eye, including, without limitation, proliferative vitreo-retinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising a compound of Formula 7 in admixture with a pharmaceutically acceptable excipient.

In another aspect, this invention relates to processes for making a compound of Formula 7 which process comprises reacting a compound of Formula 8 with a compound of Formula 9, in the presence of cuprous iodide and Pd(PQ$_3$)$_2$C$_{12}$ (Q is phenyl) or a similar complex, or reacting the zinc salt of the compound shown in Formula 8 with a compound of Formula 9 in the presence of Pd(PQ$_3$)$_4$ (Q is phenyl) or similar complex. In Formula 8 the symbol SDHN represents a dihydronaphthalene nucleus which is appropriately substituted to provide the compounds defined in Formula 7, or said dihydronaphthalene nucleus is appropriately substituted to provide such precursors of compounds of the Formula 7 from which the target compounds can be readily obtained by organic reactions well known in the art. In Formula 9 X$_1$ is halogen, B' is H, or a protected acid, alcohol, aldehyde, or ketone. In effect, B' is either the desired B group of Formula 7, or B' is a precursor from which the B group can be readily obtained by reactions well known in the art.

Formula 8        Formula 9

Still further, the present invention relates to such reactions performed on the compounds of Formula 7 which cause transformations of the A—B group or of the substituents on the dihydronaphthalene moiety, while the reaction product still remains within the scope of Formula 7.

GENERAL EMBODIMENTS

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B (of Formula 7) is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_1$, where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula —CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis (E and Z) isomers. In addition, the compounds of the present invention may contain one or more chiral centers and therefore may exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well. In the present application when no specific mention is made of the configuration (cis, trans or R or S) of a compound (or of an asymmetric carbon) then a mixture of such isomers, or either one of the isomers is intended.

Referring now to the nomenclature used in naming the compounds of the invention and intermediate compounds leading thereto, two different systems for numbering the tetrahydronaphthalene ring are demonstrated as shown by the structural formulas of Compounds F, G and 1. Compound 1 and Compounds F and G are exemplary intermediates utilized in the synthesis of the compounds of the invention. The numbering systems illustrated here will not only be readily apparent to those skilled in the art, but will be readily understood as it is applied in the ensuing description of the compounds of the invention and of intermediates utilized for obtaining the compounds of the invention.

Compound F

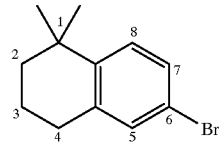

Compound G

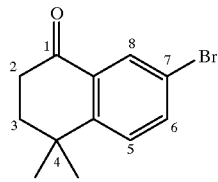

Compound 1

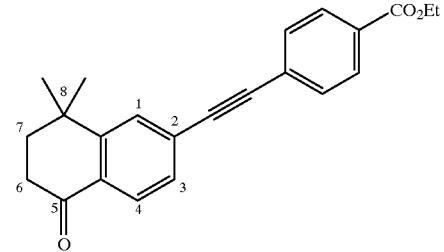

With reference to the symbol Y in Formula 7, the preferred compounds of the invention are those where Y is phenyl, pyridyl, thienyl or furyl. Even more preferred are compounds where Y is phenyl or pyridyl. As far as substitutions on the Y (phenyl) and Y (pyridyl) groups are concerned, compounds are preferred where the phenyl group is 1,4 (para) substituted, and where the pyridine ring is 2,5 substituted. (Substitution in the 2,5 positions in the "pyridine" nomenclature corresponds to substitution in the 6-position in the "nicotinic acid" nomenclature.) In the preferred compounds of the invention there is no optional R$_2$ substituent on the Y group.

The A—B group of the preferred compounds is (CH$_2$)$_n$—COOH or (CH$_2$)$_n$—COOR$_8$, where R$_8$ is defined as above. Even more preferably n is zero and R$_8$ is lower alkyl.

The aromatic portion of the tetrahydronaphthalene or dihydronaphthalene moiety is preferably substituted only by the acetylene function. In other words, in the preferred compounds there is no $R_2$ substituent (other than hydrogen). Similarly, in the preferred compounds of the invention there is no $R_3$ substituent (other than hydrogen). The $R_1$ substituent of the compounds of the invention is preferably lower alkyl, and even more preferably methyl.

In the preferred compounds of the invention $R_{22}$ is preferably hydrogen, alkyl of 1–10 carbons, alkynyl of 2 to 10 carbons having 1 triple bond, alkylphenyl having 1 to 10 carbons in the alkyl group, phenylalkyl having 1 to 10 carbons in the alkyl group, phenylalkynyl having 2 to 10 carbons in the alkynyl group, $CH_2CO_2R_8$, hydroxyalkyl having 1 to 10 carbons in the alkyl group, hydroxyalkynyl having 2 to 10 carbons in the alkynyl group, cyano (CN), $CONH_2$ or heteroaryl. Among the heteroaryl groups 5 or 6 membered rings having 1 or 2 heteroatoms are particularly preferred. Compounds where the $R_{22}$ group is 2-thiazolyl, 2-furyl, 2-thienyl or 2-pyridyl are especially preferred. Specific preferred compounds of the invention and their synthesis are described below in the section of this application titled "Specific Examples". The presently most preferred compounds of the invention in accordance with Formula 7 are indicated in Table 1 below, with reference to Formula 7A. The numbering system used for the compounds of the invention is in accordance with the example shown above for Compound 1.

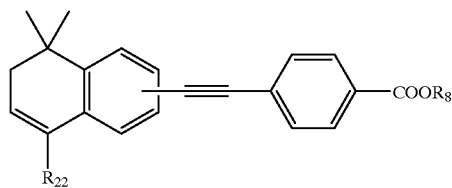

Formula 7A

TABLE 1

| Compound No. | Position of Ethynyl Substituent | $R_8$ | $R_{22}$ |
|---|---|---|---|
| 67 | 3 | Et | 2-thiazolyl |
| 69 | 3 | Et | 4-t-butylphenyl |
| 70 | 3 | Et | 2-pyridyl |
| 71 | 3 | Et | t-butyl |
| 72 | 3 | Et | H |
| 73 | 3 | Et | $CH_3$— |
| 74 | 3 | Et | $CH_3(CH_2)_3$— (n-butyl) |
| 76 | 3 | Et | 1-(3,3-dimethyl)butynyl- |
| 77 | 3 | Et | $CH_3CC$— (1-propynyl) |
| 78 | 3 | H | 2-thiazolyl |
| 79 | 3 | H | phenyl |
| 80 | 3 | H | t-butyl |
| 81 | 3 | H | H |
| 82 | 3 | H | methyl |
| 83 | 3 | H | $CH_3(CH_2)_3$— (n-butyl) |
| 84 | 3 | H | $CH_3(CH_2)_2CC$— (1-pentynyl) |
| 85 | 3 | H | 1-(3,3-dimethyl)butynyl- |
| 86 | 3 | H | $CH_3CC$— (1-propynyl) |
| 88 | 2 | Et | 2-thiazolyl |
| 89 | 2 | Et | phenyl |
| 90 | 2 | Et | phenylethynyl |
| 91 | 2 | Et | 1-(3-hydroxy-3-methyl)butynyl |
| 92 | 2 | Et | $CH_3CC$— (1-propynyl) |
| 93 | 2 | Et | $CH_2(CH_2)_2CC$— (1-pentynyl) |
| 94 | 2 | Et | 1-(3,3-dimethyl)butynyl |

TABLE 1-continued

| Compound No. | Position of Ethynyl Substituent | $R_8$ | $R_{22}$ |
|---|---|---|---|
| 95 | 2 | Et | methyl |
| 96 | 2 | Et | t-butyl |
| 97 | 2 | H | phenyl |
| 98 | 2 | H | phenylethyn-1-yl |
| 99 | 2 | H | 1-(3-hydroxy-3-methyl)butynyl |
| 100 | 2 | H | $CH_3CC$— (1-propynyl) |
| 101 | 2 | H | 1-(3,3-dimethyl)butynyl |
| 102 | 2 | H | methyl |
| 103 | 2 | H | t-butyl |
| 104 | 2 | H | 2-thiazolyl |
| 108 | 2 | Et | CN |
| 109 | 2 | Et | $CONH_2$ |
| 110 | 2 | Et | H |
| 114 | 2 | Et | $CH_2CO_2Et$ |
| 120 | 3 | Et | $CH_2CO_2Et$ |
| 122 | 3 | Et | 2-furyl |
| 123 | 3 | Et | 2-thienyl |
| 124 | 3 | H | 2-furyl |
| 125 | 3 | H | 2-thienyl |
| 129 | 3 | H | CN |
| 130 | 2 | H | CN |
| 163 | 3 | Et | 4-Mephenyl |
| 164 | 3 | H | 4-Mephenyl |

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per mililiter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

Assay of Retinoid-like Biological Activity

The retinoic acid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-O-tetradecanoylphorbol-13-acetate (TPA) induces ODC activity. Retinoic acid inhibits this induction of ODC activity by TPA. An assay essentially following the procedure set out in Cancer Research: 1662–1670, 1975 may be used to demonstrate inhibition of TPA induction of ODC by compounds of this invention. Activity of exemplary compounds of the present invention in the above-described ODC assay is disclosed in Table 2 which provides the $IC_{80}$ concentration for the respective exemplary compound. ("$IC_{80}$" is that concentration of the test compound which causes 80% inhibition in the ODC assay. By analogy, "$IC_{60}$, for example, is that concentration of the test compound which causes 60% inhibition in the ODC assay.)

TABLE 2

| Compound # | $IC_{80}$ conc (nmols) |
|---|---|
| 67 | 56.70 |
| 71 | 3.3 |
| 74 | <0.3 |
| 76 | 100* ($IC_{71}$) |
| 77 | 95 |
| 88 | 0.48 |
| 89 | <3 |
| 90 | 25 |
| 91 | 5.70 |
| 92 | 1.04 |
| 93 | <3 |
| 94 | 77.2 |
| 108 | 0.79 |
| 109 | 26.00 |
| 110 | 0.6 |
| 114 | 1.61 |
| 120 | <1 |

*the inhibition shown in brackets was attained at this concentration.

SPECIFIC EMBODIMENTS

The compounds of this invention can be made by the synthetic chemical pathways illustrated here. The synthetic chemist will readily appreciate that the conditions set here are specific embodiments which can be generalized to any and all of the compounds represented by Formula 7.

Reaction Scheme 1

SYNTHESIS

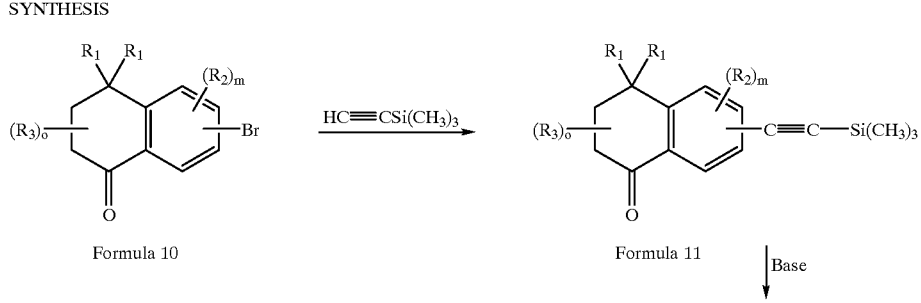

Formula 10     Formula 11 ↓ Base

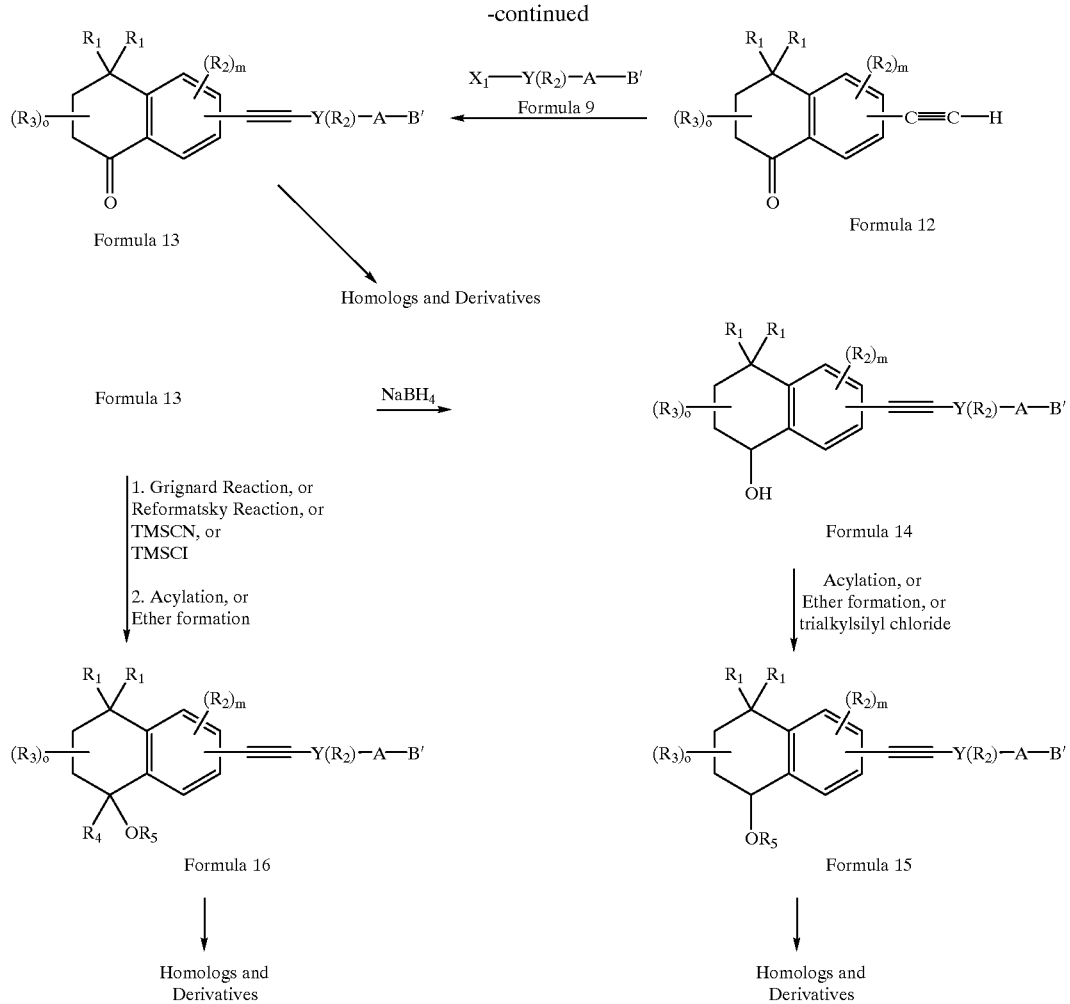

Referring now to Reaction Scheme 1 a synthetic route leading to precursors to compounds of the invention is illustrated. In accordance with this scheme, a 6- or 7-bromo substituted 3,4-dihydro-naphthalen-1(2H)-one (numbering as shown for Compound G) of Formula 10 is the starting material. The compounds of Formula 10 already carry the desired $R_1$, $R_2$ and $R_3$ substituents, as these are defined above in connection with Formula 7. The compounds of Formula 10 are reacted with (trimethylsilyl)acetylene to provide the 6- or 7-(trimethylsilyl)ethynyl-substituted 3,4-dihydro-naphthalen-1(2H)-one compounds of Formula 11. The reaction with (trimethylsilyl)acetylene is typically conducted under heat (approximately 100° C.) in the presence of cuprous iodide, a suitable catalyst, typically having the formula $Pd(PPh_3)_2Cl_2$, an acid acceptor (such as triethylamine) under an inert gas (argon) atmosphere. Typical reaction time is approximately 24 hours. The 6- or 7-(trimethylsilyl)ethynyl-substituted 3,4-dihydro-naphthalen-1(2H)-one compounds of Formula 11 are then reacted with base (potassium hydroxide or potassium carbonate) in an alcoholic solvent, such as methanol, to provide the 6- or 7-ethynyl substituted 3,4-dihydro-1-naphthalen-1(2H)ones of Formula 12. Compounds of Formula 12 are then coupled with the aromatic or heteroaromatic reagent $X_1$—Y($R_2$)—A—B' (Formula 9) in the presence of cuprous iodide, a suitable catalyst, typically $Pd(PPh_3)_2Cl_2$, an acid acceptor, such as triethylamine, under inert gas (argon) atmosphere. Alternatively, a zinc salt (or other suitable metal salt) of the compounds of Formula 12 can be coupled with the reagents of Formula 9 in the presence of $Pd(PPh_3)_4$ or similar complex. Typically, the coupling reaction with the reagent $Z_1$—Y($R_2$)—A—B' (Formula 9) is conducted at room or moderately elevated temperature. Generally speaking, coupling between an ethynylaryl derivative or its zinc salt and a halogen substituted aryl or heteroaryl compound, such as the reagent of Formula 9, is described in U.S. Pat. No. 5,264,456, the specification of which is expressly incorporated herein by reference. The compounds of Formula 13 are precursors to compounds of the invention or a derivative thereof protected in the B' group, from which the protecting group can be readily removed by reactions well known in the art. The compounds of Formula 13 can also be converted into further precursor compounds of the invention by such reactions and transformations which are well known in the art. Such reactions are indicated in Reaction Scheme 1 by conversion into "homologs and derivatives". One such conversion employed for the synthesis of several exemplary compounds of this invention is saponification of an ester group (when B or B' is an ester) to provide the free carboxylic acid or its salt.

The halogen substituted aryl or heteroaryl compounds of Formula 9 can, generally speaking, be obtained by reactions well known in the art. An example of such compound is ethyl 4-iodobenzoate which is obtainable, for example, by esterification of 4-iodobenzoic acid. Another example is ethyl 6-iodonicotinoate which can be obtained by conducting a halogen exchange reaction on 6-chloronicotinic acid, followed by esterification. Even more generally speaking, regarding derivatization of compounds of Formula 13 and/or the synthesis of aryl and heteroaryl compounds of Formula 9 which can thereafter be reacted with compounds of Formula 12, the following well known and published general principles and synthetic methodology can be employed.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups,* Ed. Greene, John Wiley & Sons, 1981.

To increase the value of n in the compounds of Formula 9 before affecting the coupling reaction of Reaction Scheme 1 (where such compounds corresponding to Formula 9 are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

Compounds of Formula 9, (or other intermediates or of the invention, as applicable) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of Formula 9 (or other intermediates or of the invention, as applicable) where the A group has a triple (acetylenic) bond can be made by reaction of a corresponding aromatic methyl ketone with strong base, such as lithium diisopropylamide, reaction with diethyl chlorophosphate and subsequent addition of lithium diisopropylamide.

The acids and salts derived from compounds of Formula 13 (or other intermediates or compounds of the invention, as applicable) are readily obtainable from the corresponding esters. Basic saponification with an alkali metal base will provide the acid. For example, an ester of Formula 13 (or other intermediates or compounds of the invention, as applicable) may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.,* 399, 1979), or dimethyl sulfoxide/oxalyl chloride in methylene chloride (Omura, K., Swern, D., *Tetrahedron.* 1978. 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 9 (or other intermediates, or of the invention, as applicable) where B is H can be prepared from the corresponding halogenated aromatic or hetero aromatic compounds, preferably where the halogen is I.

Referring still to Reaction Scheme 1, the 7,8-dihydronaphthalen-5(6H)-one derivatives of Formula 13 (numbering as exemplified above for Compound 1) are reduced with a mild reducing agent such as sodium borohydride, to yield the corresponding 5-hydroxy-5,6,7,8-tetrahydronaphthalene derivatives of Formula 14. The 5-hydroxy function of the compounds of Formula 14 is then acylated with a suitable acylating agent (such as a carboxylic acid chloride or anhydride), or converted into an ether with a suitable reagent (such as an alkyl bromide under basic conditions, or dihydropyran under acidic conditions) or converted into a trialkylsilyl ether (with trialkylsilyl chloride or other "silylating" agent) to provide compounds of Formula 15. In Formula 15 $R_5$ symbolizes the acyl group, or ether forming group such as trialkylsilyl. The compounds of Formula IS can be "deprotected" or otherwise converted into further precursor compounds to the invention by reactions well known in the art, as described above.

Describing still the reactions outlined in Reaction Scheme 1, the compounds of Formula 13 can also be reacted with a Reformatsky reagent derived from an α halocarboxylic acid ester (such as ethyl bromoacetate), or with a Grignard reagent, optionally followed by acylation or ether formation on the resulting tertiary hydroxyl group on the 5-position of the tetrahydronaphthalene nucleus, to yield compounds of Formula 16. Alternatively, the compounds of Formula 13 are reacted with cyanotrimethylsilane in the presence of boron trifluoroetherate to yield compounds in accordance with Formula 16. The compounds of Formula 16 can also be converted into further homologs and derivatives as still further precursors to compounds within the scope of the invention. In Formula 16 the $R_4$ group represents the group (such as alkyl, aryl or carbalkoxyalkyl (eg $CH_2COOalkyl$) which is introduced by the Grignard or Reformatsky reaction.

With reference to the coupling reactions of the reagent $X_1$—$Y(R_2)$—A—B' (Formula 9) shown in the foregoing reaction scheme, it is noted that, generally speaking, this coupling reaction can be conducted with 6- or 7-substituted ethynyl compounds which either already have a substituent desired for the present invention in the 5-position or have a precursor suitable for introduction of such desired substituent.

Reaction Scheme 2

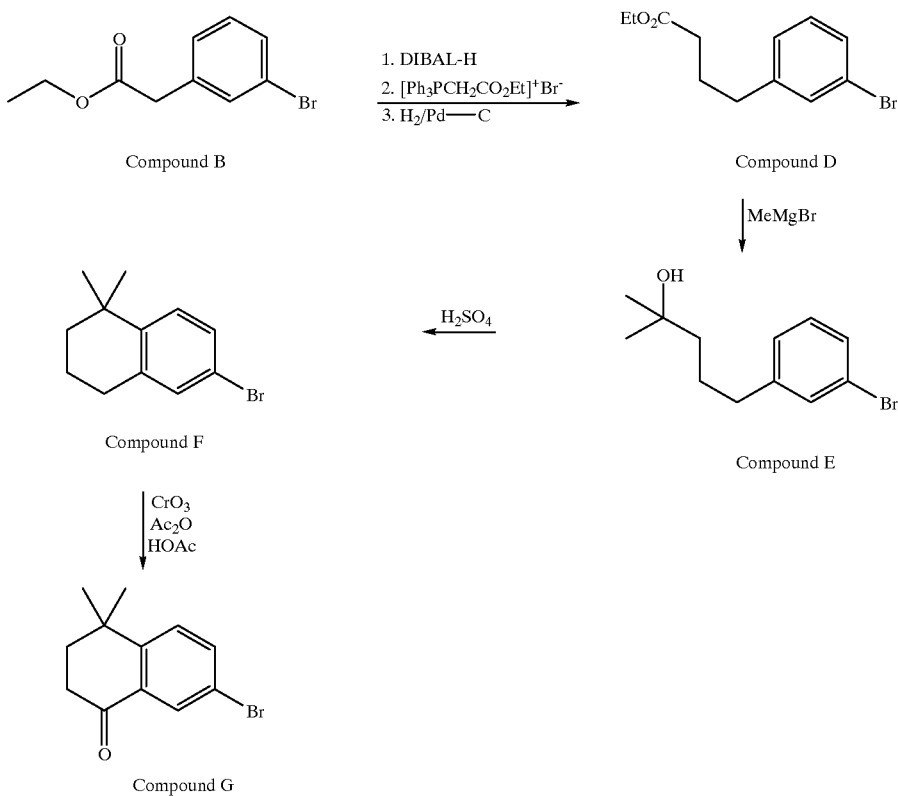

In the preferred compounds of the invention the two $R_1$ substituents are methyl, and the $R_2$ and $R_3$ substituents are hydrogen. Reaction Scheme 2 illustrates a synthetic process for preparing 7-bromo-3,4-dihydro-4,4-dimethylnaphthalen-1-one (Compound G) which serves as a starting material for the synthesis of several preferred compounds of the invention. Thus, referring now specifically to Reaction Scheme 2, ethyl 3-bromophenylacetate (Compound B, made by esterification of 3-bromophenylacetic acid) is reduced with diisobutylaluminum hydride (DIBAL-H) to yield (3-bromophenyl) acetaldehyde. (3-Bromophenyl)acetaldehyde is reacted in a Wittig reaction with (carbethoxymethylene) triphenylphosphorane to provide a mixture of E and Z ethyl 4-(3-bromophenyl)but-2-enoates. The latter compounds are hydrogenated to yield ethyl 4-(3-bromophenyl)butanoate (Compound D). Compound D is reacted with the Grignard reagent derived from methylbromide to give the tertiary alcohol 5-(3-bromophenyl)-2-methylpentan-2-ol (Compound E) (It should be apparent to those skilled in the art, that the choice of the Grignard reagent used in this reaction step determines the nature of the $R_1$ substituent in the resulting compounds of the invention.) Compound E is then treated with acid to cyclize it and to form 6-bromo-1,2,3,4-tetrahydro-1,1-dimethylnaphthalene (Compound F). Compound F is oxidized with chromium trioxide to yield 7-bromo-3,4-dihydro-4,4-dimethylnaphthalen-1(2H)-one (Compound G). Compound G is covered by Formula 10 and serves as a starting material in the synthesis of several preferred compounds of the invention.

6-Bromo-3,4-dihydro-4,4-dimethylnaphthalen-1(2H)-one (Compound H) is isomeric with Compound G, and can be obtained, starting with ethyl (4-bromophenyl)acetate, in accordance with the sequence of reactions illustrated in Reaction Scheme 2 for Compound G. 6-Bromo-3,4-dihydro-4,4-dimethylnaphthalen-1(2H)-one (Compound B) can also be obtained in accordance with the published literature procedure: Mathur et al. Tetrahedron, 41, 1509–1516 (1985). Compound H is also covered by Formula 10 and serves as a starting material in the synthesis of several preferred compounds of the invention.

Starting materials for the synthetic routes outlined in Reaction Schemes 1, 3, 4 and 5 where the $R_2$ and/or $R_3$ groups are other than hydrogen, can be obtained similarly to the synthesis of the starting materials demonstrated in Reaction Scheme 2, and/or by introducing the $R_2$ by a Friedel-Crafts or like reaction into the aromatic portion of the tetrahydronaphthalene or dihydronaphthalene nucleus.

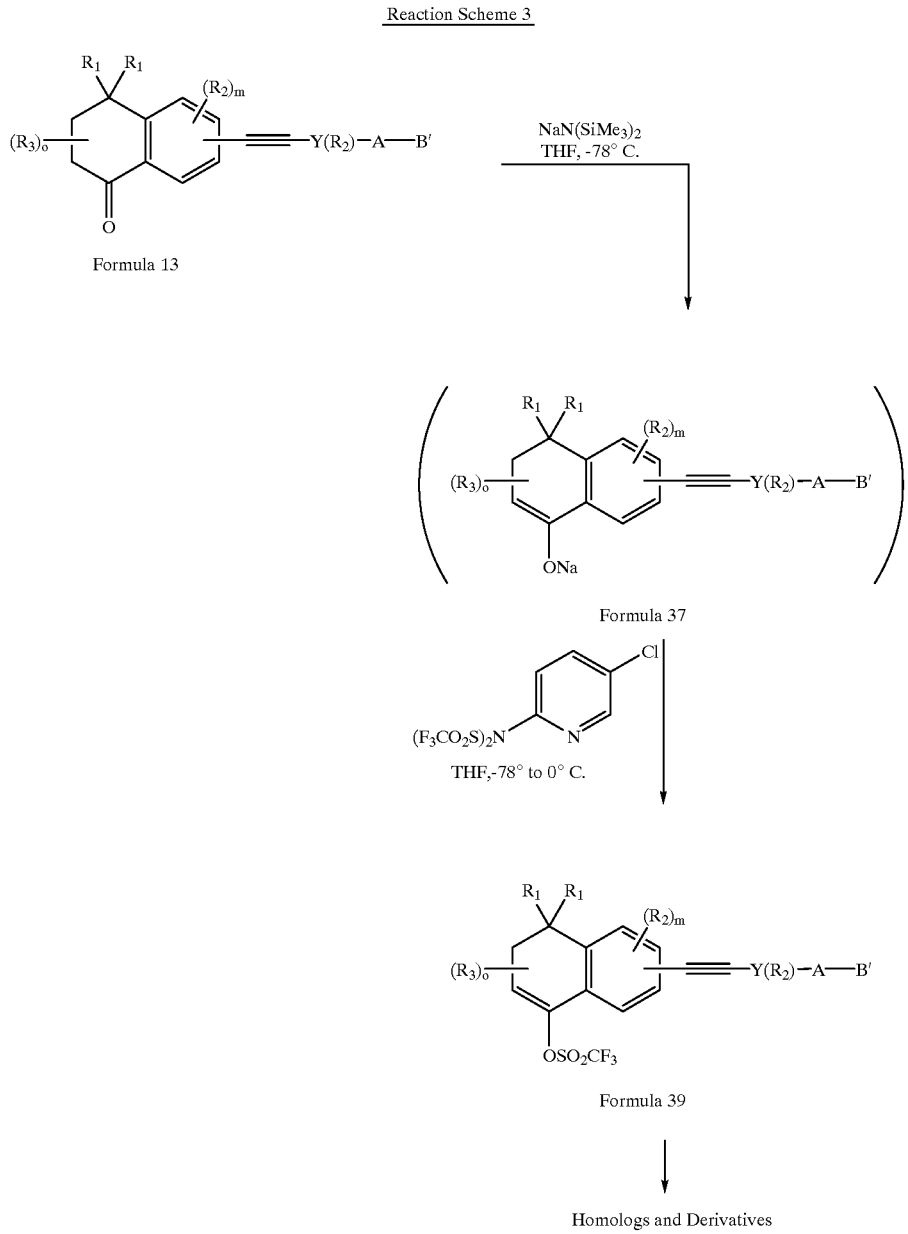

Reaction Scheme 3

Reaction Scheme 4

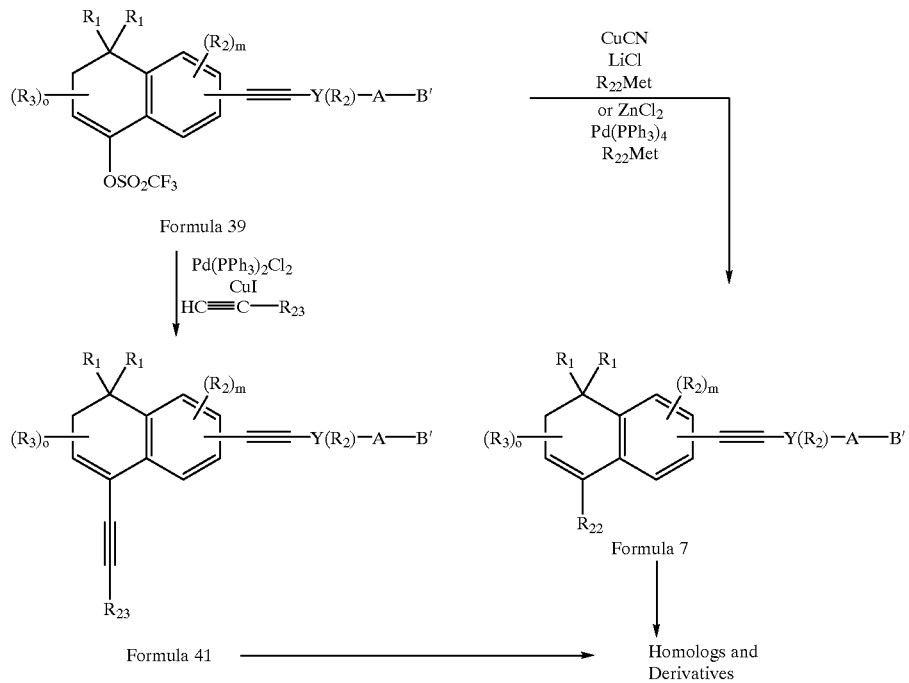

Formula 39

Formula 41

Formula 7

Homologs and Derivatives

Reaction Schemes 3 and 4 disclose synthetic steps for the preparation of those compounds of Formula 7 where the $R_{22}$ group is alkyl, alkenyl, alkynyl, carbocyclic aryl or heteroaryl, as these groups are broadly defined in Formula 7. In accordance with the presently preferred method of synthesizing these compounds of the invention, 5-trifluoromethylsulfonyloxy 2- or 3-(aryl or heteroaryl) ethynyl 7,8-dihydronaphthalene compounds of Formula 39 (numbering as exemplified for Compound 1) serve as starting materials. The compounds of Formula 39 can be obtained from the 5-oxo 2- or 3-(aryl or heteroaryl)ethynyl 5,6,7,8-tetrahydronaphthalene compounds of Formula 13 by reaction with sodium bis(trimethylsilyl)amide and 2-[N,N-bis(trifluoromethylsulfonyl)amino]-5-chloropyridine in an inert ether type solvent such as tetrahydrofuran at low temperatures (−78° C. and 0° C.). This is shown above in connection with Reaction Scheme 3.

Referring now to Reaction Scheme 4 the compounds of Formula 39 are reacted with an organometal derivative derived from the alkane, alkene, alkyne, or aryl or heteroaryl compound $R_{22}H$, such that the formula of the organometal derivative is $R_{22}Met$ (Met stands for metal), preferably $R_{22}Li$. The reaction with the organometal derivative, preferably lithium derivative of the formula $R_{22}Li$ is usually conducted in an inert ether type solvent (such as tetrahydrofuran) in the presence of either (1) cuprous cyanide (CuCN) and lithium chloride (LiCl), or in the presence of zinc chloride ($ZnCl_2$) and tetrakis(triphenylphosphine)-palladium(0) ($Pd(PPh_3)_4$). The organolithium reagent $R_{22}Li$, if not commercially available, can be prepared from the compound $R_{22}H$ (or its halogen derivative $R_{22}$—$X_1$ where $X_1$ is halogen) in an ether type solvent in accordance with known practice in the art. The temperature range for the reaction between the reagent $R_{22}Li$ and the compounds of Formula 39 is, generally speaking in the range of approximately −78° C. to 50° C. Examples of the lithium compounds which are used in the just described reaction are lithium salts derived from straight and branch chained alkanes, such as methyllithium, butyllithium, t-butyllithium, lithium salts derived from carbocyclic aryl compounds, such as phenyl-lithium, and lithium salts derived from heteroaryl compounds, such as 2-thiazolyllithium, 2-furyllithium, 2-thienyllithium, and 2-pyridyllithium. The just described synthetic process is preferably used for the synthesis of compounds of the invention within the scope of Formula 7 where the triple bonded (alkynyl) carbon is not directly attached to the 5-position of the 7,8-dihydronaphthalene nucleus. These compounds are shown in the scheme as the products of the reaction of compounds of Formula 39 with the $R_{22}Met$ (preferably $R_{22}Li$) reagent.

Referring still to Reaction Scheme 4, the presently preferred method for the synthesis of those compounds of Formula 7 is disclosed where a triple bonded (alkynyl) carbon is directly attached to the 5-position of the 7,8-dihydronaphthalene nucleus. These compounds are shown in Formula 41, where $R_{23}$ is defined as $R_{22}$ of Formula 7 minus a two carbon fragment, so that the alkyne reagent $R_{23}C{\equiv}CH$ is within the applicable definition of $R_{22}$ of Formula 7; namely $R_{23}C{\equiv}CH$ is alkynyl having 2 to 10 carbons and 1 to 3 triple bonds, phenyl-$C_1$–$C_{10}$alkynyl having 1 to 3 triple bonds, hydroxyalkynyl having 2 to 10 carbons and 1 to 3 triple bonds, acyloxyalkynyl of 2 to 10 carbons and 1 to 3 triple bonds. Compounds of Formula 41 are obtained by the reaction compounds of Formula 39 with the reagent $R_{23}C{\equiv}CH$ in an inert ether type solvent, or dimethylformamide, or without solvent, in the presence of a mild base (such as diethylamine), cuprous iodide (CuI), and bis(triphenylphosphine)palladium(II) chloride ($Pd(PPh_3)_2Cl_2$) in an inert gas (argon) atmoshere. The reaction is typically conducted in the temperature range of ambient to 70° C.

Compounds of Formula 40 and 41 can be converted into further homologs and derivatives still within the scope of the invention, as is described above in connection with compounds of Formula 13.

Referring now to Reaction Scheme 5 an alternative synthetic route for the preparation of compounds of Formula 7 is disclosed.

refluxed for 16 hours. The reaction mixture was cooled to ambient temperature, stirred with 6 g of solid $K_2CO_3$ for 30 minutes and then filtered. The filtrate was concentrated in vacuo, diluted with $Et_2O$ (200 ml), washed with 10% aqueous $NaHCO_3$ (10 ml) and brine (10 ml), dried over Reaction Scheme 5

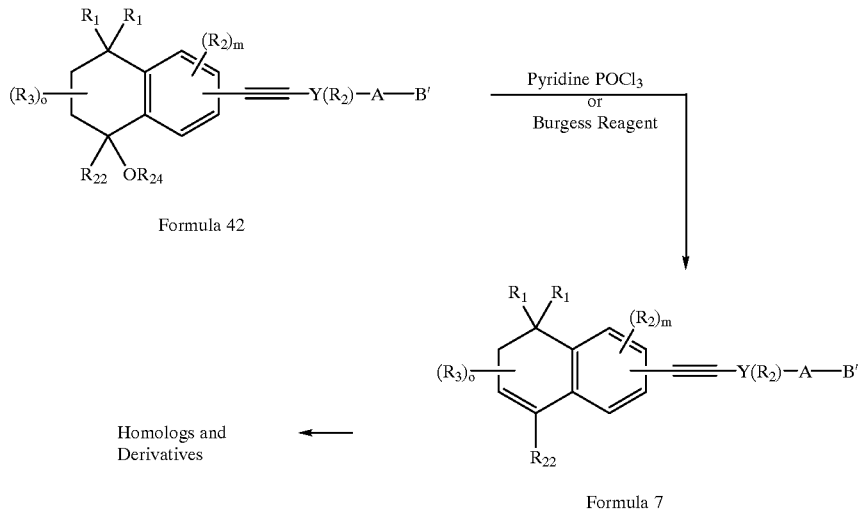

Formula 42

Formula 7

According to this reaction scheme, derivatives of 5-hydroxy, 2- or 3-(aryl or heteroaryl)ethynyl 5,6,7,8-tetrahydronaphthalene compounds of Formula 42 serve as the starting materials. Compounds of Formula 42 can be prepared as set forth in Reaction Scheme 1. Specifically, in Formula 42 the group $R_{22}$ is defined as in connection with Formula 7, and $R_{24}$ is hydrogen, or trialkylsilyl (preferably trimethylsilyl), or any other group which is suitable to form a leaving group including the $R_{24}O^-$ element, in the elimination reaction which is shown in the reaction scheme. The product of the elimination reaction is a compound of Formula 7. The reaction is conducted under conditions which are known in the art of organic chemistry to cause formation of double bonds by elimination, for example in refluxing pyridine in the presence of excess phosphorous oxychloride ($POCl_3$), or in a neutral hydrocarbon type solvent (such as benzene) in the presence of (methoxycarbonylsulfamoyl) triethylammonium hydroxide (Burgess reagent). Reaction Scheme 5 is presently preferred for the preparation of compounds of Formula 7 where the $R_{22}$ group is hydrogen, cyano (CN) and $CH_2COOEt$. The elimination reaction which results in compounds where $R_{22}$ is $CH_2COOEt$ also gives rise to isomers where the double bond is exterior to the condensed 6-membered ring. The latter compounds are not shown in this reaction scheme.

The compounds of Formula 7 can also be prepared by first forming the dihydronaphthalene derivative substituted in the 5 position with the $R_{22}$ group from the ketone compounds of Formula 10 (see Reaction Scheme 1) and thereafter performing the synthetic steps of replacing, the 6 or 7-bromo substituents in these compounds with an ethynyl group, and subsequently coupling the ethynyl compounds with the reagent $X_1$—$Y(R_2)$—$A$—$B'$ (Formula 9).

SPECIFIC EXAMPLES

Ethyl (4-bromophenyl)acetate (Compound A)

A solution of 43 g (200 mmol) of 4-bromophenylacetic acid and 0.2 g of conc. $H_2SO_4$ in 470 ml of ethanol was $MgSO_4$ and concentrated in vacuo to give the title compound as a colorless oil.

PMR ($CDCl_3$): δ1.25 (3H, t, J=7.0 Hz), 3.56 (2H, s), 4.15 (2H, q, J=7.0 Hz), 7.16 (2H, d, J=8.4 Hz), 7.45 (2H, d, J=8.4 Hz).

Ethyl (3-bromophenyl)acetate (Compound B)

Employing the same general procedure as for the preparation of ethyl (4-bromophenyl)acetate (Compound A), 100 g (463 mmol) of 3-bromophenylacetic acid was converted into the title compound (yellow oil) using 2 g of conc. $H_2SO_4$ and 500 ml of ethanol.

PMR ($CDCl_3$): δ1.26 (3H, t, J=7.0 Hz), 3.56 (2H, s), 4.16 (2H, q, J=7.0 Hz), 7.16–7.26 (2H, m), 7.38–7.46 (2H, m).

Ethyl 4-(4-bromophenyl)butanoate (Compound C)

To a cold solution (−78° C.) of 15 g (62 mmol) of ethyl (4-bromophenyl)acetate (Compound A) in 150 ml of $CH_2Cl_2$ was added dropwise (over a span of 1 hour) 65 ml (65 mmol) of diisobutylaluminum hydride (DIBAL-H, 1M solution in hexane). After the DIBAL-H addition was complete, the reaction was stirred at −78° C. for an additional hour. The reaction was quenched by the dropwise addition of methanol (10 ml), followed by water (10 ml) and 10% HCl (40 ml). The mixture was then warmed to 0° C., stirred for 10 minutes and then washed with water (15 ml), 10% aqueous $NaHCO_3$ (10 ml) and brine (10 ml). The organic phase was dried over $MgSO_4$ and the solvent distilled off at ambient temperature to give crude (4-bromophenyl)acetaldehyde. To a cold solution (0° C.) of this crude aldehyde in 150 ml of $CH_2Cl_2$ was added a solution of 26 g (74.6 mmol) of (carbethoxymethylene) triphenylphosphorane in 50 ml of $CH_2Cl_2$. The mixture was stirred for 16 hours, concentrated in vacuo and purified by flash chromatography (silica, 10% EtOAc-hexane) to give ethyl 4-(4-bromophenyl)but-2-enoate as a mixture of E:Z isomers. This isomeric mixture was dissolved in 150 ml of EtOAc and hydrogenated over 1 g of 10% Pd/C for 6 hours. The catalyst was filtered off and the filtrate concentrated in vacuo to give the title compound as a white solid.

PMR (CDCl$_3$): δ1.26 (3H, t, J=7.1 Hz), 1.88–1.99 (2H, m), 2.31 (2H, t, J=7.5 Hz), 2.61 (2H, t, J=7.5 Hz), 4.28 (2H, q, J=7.1 Hz), 7.05 (2H, d, J=8.4 Hz), 7.40(2H, d, J=8.4 Hz).

Ethyl 4-(3-bromophenyl)butanoate (Compound D)

Employing the same general multistep preparation as for ethyl 4-(4-bromophenyl)butanoate (Compound C), 60 g (246 mmol) of ethyl (3-bromophenyl)acetate (Compound B) was converted into the title compound (oil) using 255 ml (255 mmol) of diisobutylaluminum hydride (DIBAL-H, 1M in hexane), 85.8 g (250 mmol) of (carbethoxymethylene) triphenylphosphorane and 1.7 g of 10% Pd/C.

PMR (CDCl$_3$): δ1.26 (3H, t, J=7.1 Hz), 1.89–2.00 (2H, m), 2.31 (2H, t, J=7.5 Hz), 2.63 (2H, t, J=7.2 Hz), 4.15 (2H, q, J=7.1 Hz), 7.10–7.35 (4H, m).

5-(3-bromophenyl)-2-methylpentan-2-ol (Compound E)

To a cold solution (0° C.) of 17 g (63 mmol) of ethyl 4-(3-bromophenyl)butanoate (Compound D) in 40 ml of THF was added 63 ml (189 mmol) of methylmagnesium bromide (3.0M solution in THF). The reaction was stirred at 0° C. for 2 hours, quenched by the slow addition of ice cold water (30 ml) followed by 10% HCl (30 ml) and then extracted with Et$_2$O (4×60 ml). The combined organic layer was washed with 10% aqueuos NaHCO$_3$ (10 ml), water (10 ml) and brine (10 ml), dried over MgSO$_4$ and concentrated in vacuo. Purification by Kugelrohr distillation gave the title compound as a colorless oil.

PMR (CDCl$_3$): δ1.20 (6H, s), 1.43–1.55 (2H, m), 1.62–1.78 (2H, m), 2.60 (2H, t, J=6.0 Hz), 7.10–7.41 (4H, m).

6-Bromo-1,2,3,4-tetrahydro-1,1-dimethylnaphthalene (Compound F)

15.0 g (58.3 mmol) of 5-(3-bromophenyl)-2-methylpentan-2-ol (Compound E) was cooled to 0° C. and then 2.8 ml of conc. H$_2$SO$_4$ was added. The mixture was stirred for 2.5 hours, diluted with water (20 ml) and extracted with Et$_2$O (3×40 ml). The combined organic layers were washed with water, sat. aqueous NaHCO$_3$ and brine, dried over MgSO$_4$ and concentrated in vacuo. Purification by Kugelrohr distillation gave the title compound as a colorless oil.

PMR (CDCl$_3$): δ1.25 (6H, s), 1.61–1.66 (2H, m), 1.74–1.82 (2H, m), 2.73 (2H, t, J=6.0 Hz), 7.16–7.26 (3H, m).

7-Bromo-3,4-dihydro-4,4-dimethylnaphthalen-1 (2H)-one (Compound G)

To a cold mixture (0° C.) of 209 g (200 mmol) of chromium trioxide, 100 ml (1.06 mol) of acetic anhydride and 200 ml (3.5 mol) of acetic acid was added a solution of 10 g (41.8 mmol) of 6-bromo-1,2,3,4-tetrahydro-1,1-dimethylnaphthalene (Compound F) in 125 ml of benzene. The reaction mixture was stirred for 1 hour, quenched with ice cold water and extracted with Et$_2$O (3×100 ml). The organic layer was dried over MgSO$_4$, concentrated in vacuo, and purified by column chromatography (silica, 10% EtOAc-hexane) to give the title compound as a white solid.

PMR (CDCl$_3$): δ1.28 (6H, s), 2.01 (2H, t, J=6.0 Hz), 2.72 (2H, t, J=6.0 Hz), 7.31 (1H, d, J=9.0 Hz), 7.61 (1H, dd, J=3.0, 9.0 Hz), 8.11 (1H, d, J=3.0 Hz).

6-Bromo-3,4-dihydro-4,4-dimethylnaphthalen-1 (2H)-one (Compound H)

Employing a published procedure (Mathur, N.C.; Snow, M. S.; Young, K. M.; and Pincock, J. A. *Tetrahedron*, 41, 1509–1516 (1985) ), ethyl 4-(4-bromophenyl)butanoate (Compound C) was converted into the title compound. Alternatively, the title compound can be obtained using similar reactions that were used to convert ethyl 4-(3-bromophenyl)butanoate (Compound D) into 7-bromo-3,4-dihydro-4,4-dimethylnaphthalen-1(2H)-one (Compound G).

6-Ethynyl-3,4-dihydro-4,4-dimethylnaphthalen-1 (2H)-one (Compound K)

To a solution (flushed for 15 minutes with a stream of argon) of 13.55 g (53.8 mmol) of 6-bromo-3,4 -dihydro-4, 4-dimethylnaphthalen-1(2H)-one (Compound H) in 280 ml of triethylamine was added 1.87 g (2.66 mmol) of bis (triphenylphosphine)palladium(II) chloride and 0.53 g (2.66 mmol) of cuprous iodide. The solution mixture was flushed with argon for 5 minutes and then 100 ml (938.7 mmol) of (trimethylsilyl)acetylene was added. The reaction mixture was sealed in a pressure tube and placed in a preheated oil bath (100° C.) for 24 hours. The reaction mixture was then filtered through Celite, washed with Et$_2$O and the filtrate concentrated in vacuo to give crude 6-(trimethylsilyl) ethynyl-3,4-dihydro-4,4-dimethylnaphthalen-1(2H)-one. To a solution of this crude TMS-acetylenic compound in 50 ml of methanol was added 2.8 g (20.3 mmol) of K$_2$CO$_3$. The mixture was stirred for 8 hours at ambient temperature and then filtered. The filtrate was concentrated in vacuo, diluted with Et$_2$O (100 ml), washed with water (10 ml), 10% HCl (10 ml) and brine (10 ml), dried over MgSO$_4$ and concentrated in vacuo. Purification by column chromatography (silica, 10% EtOAc-hexane) yielded the title compound as a white solid.

PMR (CDCl$_3$): δ1.38 (6H, s), 2.01 (2H, t, J=7.1 Hz), 2.72 (2H, t, J=7.1 Hz), 3.24 (1H, s), 7.39 (1H, dd, J=1.5, 8.1 Hz), 7.54 (1H, d, J=1.5 Hz), 7.91 (1H, d, J=8.1 Hz).

7-Ethynyl-3,4-dihydro-4,4-dimethylnaphthalen-1 (2H)-one (Compound L)

Employing the same general procedure as for the preparation of 6-ethynyl-3,4-dihydro-4,4-dimethyl-naphthalen-1 (2H)-one (Compound K), 7 g (27.6 mmol) of 7-bromo-3,4-dihydro-4,4-dimethylnaphthalen-1(2H)-one (Compound G) was converted into the title compound using 39 ml (36.6 mmol) of (trimethylsilyl)acetylene, 0.97 g (1.3 mmol) of bis(triphenylphosphine)palladium(II) chloride, 0.26 g (1.3 mmol) of cuprous iodide and 0.6 g (4.3 mmol) of K$_2$CO$_3$.

PMR (CDCl$_3$): δ1.39 (6H, s), 2.02 (2H, t, J=7.0 Hz), 2.73 (2H, t, J=7.0 Hz), 3.08 (1H, 5), 7.39 (1H, d, J=8.2 Hz), 7.61 (1H, dd, J=1.8 , 8.2 Hz), 8.14 (1H, d, J=9 1.8 Hz).

Ethyl-4-iodobenzoate

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated NaHCO$_3$ and saturated NaCl solutions and dried (MgSO$_4$). Solvent was then removed in vacuo and the residue Kugelrohr distilled (100 degrees C.; 0.55 mm) to give the title compound as a colorless oil, PMR (CDCl$_3$): δ1.42 (3H, t, J-7 Hz), 4,4 (2H, q, J-7 Hz), 7.8 (4H).

Ethyl 6-chloronicotinate

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine in 200 ml methylene chloride was heated at reflux for 2 hours. The mixture was allowed to cool, solvent removed in vacuo and the residue subjected to flash chromatography to give the title compound as a low-melting white solid. PMR (CDCl$_3$): δ1.44 (3H, t, J-6.2 Hz) 4.44 (2H, q, J-4.4 Hz), 7.44 (1H, d, J-8.1 Hz), 8.27 (1H, dd, J-8.1 Hz, 3 Hz), 9.02 (1H, d, J-3 Hz).

6-Iodonicotinic Acid

To 27.97 g (186.6 mmol) of sodium iodide cooled to −78° C. was added 121.77 g (71.6 ml, 952.0 mmol) of hydriodic acid (57 wt %). The reaction mixture was allowed to warm slightly with stirring for 5 minutes, and then 30.00 g (190.4 mmol) of 6-chloronicotinic acid was added. The resulting mixture was allowed to warm to room temperature with stirring and then heated at 120–125° C. in an oil bath for 42 hours. A dark brown layer formed above the yellow solid material. The reaction mixture was allowed to cool to room temperature and then poured into acetone (chilled to 0° C.). The resultant yellow solid was collected by filtration, washed with 200 ml of 1N NaHSO$_3$ solution, and dried in high vacuum (3 mm Hg) to give the title compound as a pale yellow solid.

PMR (DMSO-d$_6$): δ7.90 (1H, dd, J=8.1, 2 Hz), 7.99 (1H, d, J=8.1 Hz), 8.80 (1H, d, J=2. Hz).

Ethyl 6-iodonicotinate

To a suspension of 23.38 g (94.2 mmol) of 6-iodonicotinic acid in 100 ml of dichloromethane was added a solution of 19.86 g (103.6 mmol) of 1-(3-dimethylaminopropyl)-3-ethylcarbodiimide hydrochloride in 250 ml of dichloromethane. To this suspension was added 12.40 g (15.8 ml, 269.3 mmol) of ethanol (95%) and 1.15 g (9.4 mmol) of 4-dimethylaminopyridine. The resulting solution mixture was then heated at 50° C. in an oil bath for 24.5 hours, concentrated in vacuo, partitioned between 200 ml of water and 250 ml of ethyl ether, and the layers were separated. The aqueous phase was washed with 2×150 ml-portions of ethyl ether. All organic phases were combined, washed once with 75 ml of brine solution, dried over MgSO$_4$, filtered and concentrated in vacuo to a yellow solid. Purification by flash chromatography (silica, 10% ethyl acetate in hexane) yielded the title compound as a white solid.

PMR (CDCl$_3$): δ1.41 (3H, t, J=7.1 Hz), 4.41 (2H, q, J=7.1 Hz), 7.85 (1H, d, J=8.2 Hz), 7.91 (1H, dd, J=8.2, 2.1 Hz), 8.94 (1H, d, J=2.1 Hz).

Ethyl 4-[(5,6,7,8-tetrahydro-8,8-dimethyl-5-oxonaphth-2-yl)ethynyl]benzoate (Compound 1)

To a solution of 8.8 g (47.8 mmol) of 6-ethynyl-1,2,3,4-tetrahydro-4,4-dimethylnaphthalen-1-one (Compound K) flushed for 15 minutes with a stream of argon, and 13.2 g (47.8 mmol) of ethyl 4-iodobenzoate in 200 ml of triethylamine was added 1.1 g (1.6 mol) of bis(triphenylphosphine) palladium(II) chloride and 0.30 g (1.6 mmol) of cuprous iodide. The solution mixture was flushed with argon for 5 minutes and then stirred at ambient temperature for 18 hours. The reaction mixture was filtered through Celite and the filtrate concentrated in vacuo. Purification by flash chromatography (silica, 10% EtOAc-hexane) yielded the title compound as a white solid.

PMR (CDCl$_3$): δ1.41 (3H, t, J=7.2 Hz), 1.43 (6H, s), 2.04 (2H, t, J=7.0 Hz), 2.75 (2H, t, J=7.0 Hz), 4.40 (2H, q, J=7.2 Hz), 7.46 (1H, dd, J=1.5, 8.1 Hz), 7.60 (1H, d, J=1.5 Hz), 7.63 (2H, d, J=8.4 Hz), 8.01 (1H, d, J=8.1 Hz), 8.05 (2H, d, J=8.4 Hz).

Ethyl 4-[(5,6,7,8-tetrahydro-8,8-dimethyl-5-oxonaphth-3-yl)ethynyl]benzoate (Compound 2)

Employing the same general procedure as for the preparation of ethyl 4-[(5,6,7,8-tetrahydro-8,8-dimethyl-5-oxonaphth-2-yl)ethynyl]benzoate (Compound 1), 4 g (21.7 mmol) of 7-ethynyl-3,4-dihydro-4,4-dimethylnaphthalen-1 (2H)-one (Compound L) was converted into the title compound using 6 g (21.7 mmol) of ethyl 4-iodobenzoate, 5 g (7.2 mmol) of bis(triphenylphosphine)palladium(II) chloride and 1.4 g (7.2 mmol) of cuprous iodide.

PMR (CDCl$_3$): δ1.41 (3H, t, J=7.2 Hz), 1.41 (6H, s), 2.04 (2H, t, J=6.5 Hz), 2.76 (2H, t, J=6.5 Hz), 4.40 (2H, q, J=7.2 Hz), 7.44 (1H, d, J=8.2 Hz), 7.59 (2H, d, J=8.4 Hz), 7.68 (1H, dd, J=1.8, 8.2 Hz), 8.04 (2H, d, J=8.4 Hz), 8.15 (1H, d, J=1.8 Hz).

Ethyl 6-[(5,6,7,8-tetrahydro-8,8-dimethyl-5-oxonaphth-3-yl)ethynyl]nicotinate (Compound 3)

Employing the same general procedure as for the preparation of ethyl 4-[(5,6,7,8-tetrahydro-8,8-dimethyl-5-oxonaphth-2-yl)ethynyl]benzoate (Compound 1), 606 mg (3.48 mmol) of 7-ethynyl-3,4-dihydro-4,4-dimethylnaphthalen-1(2H)-one (Compound K) was converted into the title compound using 964 mg (3.48 mmol) of ethyl 6-iodonicotinate, 122 mg (0.17 mmol) of bis (triphenylphosphine)palladium(II) chloride and 9.5 mg (0.17 mmol) of cuprous iodide.

PMR (CDCl$_3$): δ1.41 (6H, s), 1.43 (3H, t, J=7.1 Hz), 2.05 (2H, t, J=7.1 Hz), 2.76 (2H, t, J=7.1 Hz), 4.43 (2H, q, J=7.1 Hz), 7.46 (1H, d, J=8.2 Hz), 7.60 (1H, d, J=7.8 Hz), 7.75 (1H, dd, J=1.9, 8.2 Hz), 8.27 (1H, d, J=1.9 Hz), 8.30 (1H, dd, J=2.0, 7.8 Hz), 9.22 (1H, br s).

Ethyl 6-[(5,6,7,8-tetrahydro-8,8-dimethyl-5-oxonaphth-2-yl)ethynyl]nicotinate (Compound 5)

Employing the same general procedure as for the preparation of ethyl 4-[5,6,7,8-tetrahydro-8,8-dimethyl-5-oxonaphth-2-yl)ethynyl]benzoate (Compound 1), 422 mg (2.1 mmol) of 6-ethynyl-3,4-dihydro-4,4-dimethylnaphthalen-1(2H)-one (Compound L) was converted into the title compound using 202 mg (0.73 mmol) of ethyl 6 -iodonicotinate, 168mg (0.24 mmol) of bis (triphenylphosphine)palladium(II) chloride and 45.7 mg (0.24 mmol) of cuprous iodide.

PMR (CDCl$_3$): δ1.40 (6H, s), 1.42 (3H, t, J=7.1 Hz), 2.04 (2H, t, J=6.0 Hz), 2.74 (2H, t, J=6.0 Hz), 4.43 (2H, q, J=7.1 Hz), 7.51 (1H, d, J=8.4 Hz), 7.63 (1H, d, J=8.4 Hz), 7.70 (1H, s), 8.01 (1H, d, J=8.1 Hz), 8.30 (1H, d, J=8.1 Hz), 9.22 (1H, s).

4-[(5,6,7,8-tetrahydro-8,8-dimethyl-5-oxonaphth-2-yl)ethynyl]benzoic acid (Compound 7)

To a suspension of 0.30 g (0.87 mmol) of ethyl 4-[(5,6,7,8-tetrahydro-8,8-dimethyl-5-oxonaphth-2-yl)ethynyl] benzoate (Compound 1) in 4 ml of THF and 2 ml of ethanol was added 2 ml (2 mmol) of LiOH (1N aqueous solution). The reaction mixture was stirred at room temperature for 4 hours, concentrated in vacuo to near dryness, partitioned between EtOAc and 1 ml of water and acidified to pH 4 with 10% HCl. The aqueous layer was extracted with EtOAc and then the organic layer was dried over Na$_2$SO$_4$ and concentrated in vacuo to give the title compound as a light yellow solid.

PMR (DMSO-d$_6$): δ1.39 (6H, s), 1.98 (2H, t, J=7.0 Hz), 2.70 (2H, t, J=7.0 Hz), 7.54 (1H, dd, J=1.5, 8.1 Hz), 7.73

(2H, d, J=8.4 Hz), 7.77 (1H, d, J=1.5 Hz), 7.90 (1H, d, J=8.1 Hz), 8.00 (2H, d, J=8.4 Hz).

4-[(5,6,7,8-tetrahydro-8,8-dimethyl-5-oxonaphth-3-yl)ethynyl]benzoic acid (Compound 8)

Employing the same general procedure as for the preparation of 4-[(5,6,7,8-tetrahydro-8,8-dimethyl-5-oxonaphth-2-yl)ethynyl]benzoic acid (Compound 7), 500 mg (1.45 mmol) of ethyl 4-[(5,6,7,8-tetrahydro-8,8-dimethyl-5-oxonaphth-3-yl)ethynyl]benzoate (Compound 2) was converted into the title compound using 4 ml (4 mmol) of LiOH (1 N aqueous solution).

PMR (DMSO-$d_6$): δ1.37 (6H, s), 1.99 (2H, t, J=6.9 Hz), 2.71 (2H, t, J=6.9 Hz), 7.64 (1H, d, J=8.2 Hz), 7.70 (2H, d, J=8.3 Hz), 7.80 (1H, dd, J=2.0, 8.2 Hz), 7.98 (3H, m).

Ethyl 4-[(5,6,7,8-tetrahydro-5-hydroxy-8,8-dimethylnaphth-2-yl ethynyl]benzoate (Compound 9)

To a cold solution (0° C.) of 980 mg (2.8 mmol) of ethyl 4-[(5,6,7,8-tetrahydro-8,8-dimethyl-5-oxonaphth-2-yl)ethynyl]benzoate (Compound 1) in 5 ml of THF and 10 ml of ethanol was added 78 mg (2 mmol) of sodium borohydride. The mixture was stirred for 6 hours, diluted with water (10 ml) and extracted with $Et_2O$ (4×40 ml). The combined organic layers were washed with 10% HCl (5 ml), 10% aqueous $NaHCO_3$ (10 ml) and brine (10 ml), dried over MgSO4 and concentrated in vacuo to give the title compound as a white solid.

PMR ($CDCl_3$): δ1.25 (3H, s), 1.32 (3H, s), 1.38 (3H, t, J=7.2 Hz), 1.56–1.65 (1H, m),1.78–2.15 (4H, m), 4.35 (2H, q, J=7.2 Hz), 4.70 (1H, q, J=4.0 Hz), 7.33 (1H, dd, J=1.5 , 8.1 Hz), 7.41 (1H, d, J=8.1 Hz), 7.49 (1H, d, J=1.5 Hz), 7.56 (2H, d, J=8.4 Hz), 7.98 (2H, d, J=8.4 Hz).

Ethyl 4-[(5,6,7,8-tetrahydro-5-hydroxy-8,8-dimethylnaphth-3-yl)ethynyl]benzoate (Compound 10)

Employing the same general procedure as for the preparation of ethyl 4-[(5,6,7,8-tetrahydro-5-hydroxy-8,8-dimethylnaphth-2-yl)ethynyl]benzoate (Compound 9), 1 g (2.88 mmol) of ethyl 4-[(5,6,7,8-tetrahydro-8,8-dimethyl-5-oxonaphth-3-yl)ethynyl]benzoate (Compound 2) was converted into the title compound using 60 mg (1.6 mmol) of sodium borohydride.

PMR ($CDCl_3$): δ1.26 (3H, s), 1.33 (3H, s), 1.40 (3H, t, J=7.1 Hz), 1.58–1.70 (1H, m), 1.80–1.95 (2H, m), 2.04–2.14 (1H, m), 4.38 (2H, q, J=7.1 Hz), 4.72 (1H, q, J=5.1 Hz), 7.32 (1H, d, J=8.2 Hz), 7.41 (1H, dd, J=1.8, 8.2 Hz), 7.56 (2H, d, J=8.5 Hz), 7.65 (1H, d, J=1.8 Hz), 8.01 (2H, d, J=8.5 Hz).

Ethyl 6-[(5,6,7,8-tetrahydro-5-hydroxy-8,8-dimethylnaphth-3-yl)ethynyl]nicotinate (Compound 11)

Employing the same general procedure as for the preparation of ethyl 4-[(5,6,7,8-tetrahydro-5-hydroxy-8,8-dimethylnaphth-2-yl)ethynyl]benzoate (Compound 9), 700 mg (2 mmol) of ethyl 6-[(5,6,7,8-tetrahydro-8,8-dimethyl-5-oxonaphth-3-yl)ethynyl]nicotinate (Compound 4) was converted into the title compound using 60 mg (1.6 mmol) of sodium borohydride.

PMR ($CDCl_3$): δ1.26 (3H, s), 1.33 (3H, s), 1.42 (3H, t, J=7.1 Hz), 1.52–1.70 (1H, m), 1.70–1.95 (2H, m), 2.10–2.20 (1H, m), 4.40 (2H, q, J=7.1 Hz), 4.70 (1H, br s), 7.32 (1H, d, J=8.0 Hz), 7.48 (1H, d, J=7.9 Hz), 7.55 (1H, d, J=8.0 Hz), 7.84 (1H, s), 8.28 (1H, d, J=7.9 Hz), 9.20 (1H, br s).

4-[(5,6,7,8-tetrahydro-5-hydroxy-8,8-dimethylnaphth-3-yl)ethynyl]benzoic acid (Compound 41)

Employing the same general procedure as for the preparation of 4-[[5,6,7,8-tetrahydro-5(SR)-(2'(RS)-tetrahydropyranoxy)-8,8-dimethylnaphth-2-yl]ethynyl] benzoic acid (Compound 32), 272 mg (0.78 mmol) of ethyl 4-[(5,6,7,8-tetrahydro-5-hydroxy-8,8-dimethylnaphth-3-yl) ethynyl]benzoate (Compound 10) was converted into the title compound using 2 ml(2 mmol) of LiOH (1M aqueous solution).

PMR (acetone-$d_6$): δ1.28 (3H, s), 1.31 (3H, s), 1.60–1.70 (1H, m), 1.80–1.96 (2H, m), 2.00–2.12 (1H, m), 4.67 (1H, t, J=7.1 Hz), 7.42 (2H, br s), 7.67 (1H, d, J=8.2 Hz), 7.69 (1H, br s), 8.07 (2H, d, J=8.2 Hz).

4-[(5,6,7,8-tetrahydro-5-hydroxy-8,8-dimethylnaphth-2-yl)ethynyl]benzoic acid (Compound 42)

110 mg (0.31 mmol) of ethyl 4-[(5,6,7,8-tetrahydro-5-hydroxy-8,8-dimethylnaphth-2-yl)ethynyl]benzoate (Compound 9) in a mixture of THF and methanol was refluxed with 1 ml (1 mmol) of LiOH (1M aqueous solution). Thereafter the mixture was diluted with $Et_2O$:$EtOA_c$ (1:1), and acidified with aqueous HCl to pH5. The organic phase was separated, washed (water and brine), dried ($MgSO_4$) to yield the title compound.

PMR (acetone-$d_6$): δ1.28 (3H, s), 1.31 (3H, s), 1.58–1.70 (1H, m), 1.76–1.92 (2H, m), 1.98–2.10 (1H, m), 4.66 (1H, t, J=5.1 Hz), 7.35 (1H, dd, J=1.6, 7.9 Hz), 7.53 (1H, d, J=7.9 Hz), 7.65 (2H, d, J=8.1 Hz), 8.05 (2H, d, J=8.1 Hz).

6-[(5,6,7,8-tetrahydro-8,8-dimethyl-5-oxonaphth-3-yl)ethynyl]nicotinic acid (Compound 44)

Employing the same general procedure as for the preparation of 4-[[5,6,7,8-tetrahydro-8,8-dimethyl-5-oxonaphth-2-yl]ethynyl]benzoic acid (Compound 7), 300 mg (0.86 mmol) of ethyl 6-[(5,6,7,8-tetrahydro-8,8-dimethyl-5-oxonaphth-3-yl)ethynyl]nicotinate (Compound 3) was converted into the title compound (pale yellow solid) using 8.6 ml (8.6 mmol) of LiOH (1M aqueous solution).

PMR (DMSO-$d_6$): PMR δ1.38 (6H, s), 1.99 (2H, t, J=6 Hz), 2.72 (2H, t, J=6 Hz), 7.68 (1H, d, J=8.2 Hz), 7.82 (1H, d, J=8.5 Hz), 7.86 (1H, dd, J=2, 8.2 Hz), 8.04 (1H, d, J=2 Hz), 8.30 (1H, dd, J=1.9, 7.9 Hz), 9.07 (1H, d, 1.9 Hz).

Ethyl 4-[(5-trifluoromethylsulfonyloxy-7,8-dihydro-8,8-dimethylnaphth-3-yl)ethynyl]benzoate (Compound 66)

To a cold solution (−78° C.) of 291.6 mg (1.59 mmol) of sodium bis(trimethylsily)amide in 5.6 ml of THF was added a solution of 500.0 mg (1.44 mmol) of ethyl 4-[(5,6,7,8-tetrahydro-8,8-dimethyl-5-oxonaphth-3-yl)ethynyl] benzoate (Compound 2) in 4.0 ml of THF. The reaction mixture was stirred at −78° C. for 35 minutes and then a solution of 601.2 mg (1.59 mmol) of 2-[N,N-bis (trifluoromethylsulfonyl)amino]-5-chloropyridine in 4.0 ml of THF was added. After stirring at −78° C. for 1 hour, the solution was warmed to 0° C. and stirred for 2 hours. The reaction was quenched by the addition of sat. aqueous $NH_4Cl$. The mixture was extracted with EtOAc (50 ml) and the combined organic layers were washed with 5% aqueous NaOH, water, and brine. The organic phase was dried over $Na_2SO_4$ and then concentrated in vacuo to a yellow oil. Purification by column chromatography (silica, 7% EtOAc-hexanes) yielded the title compound as a colorless waxy solid.

PMR (CDCl₃): δ1.33 (6H, s), 1.43 (3H, t, J=7.1 Hz), 2.44 (2H, d, J=5.0 Hz), 4.40 (2H, q, J=7.1 Hz), 6.02 (1H, t, J=5.0 Hz), 7.32 (1H, d, J=8.0 Hz), 7.51 (2H, m), 7.60 (2H, dd, J=1.8, 8.4 Hz), 8.04 (2H, dd, J=1.8, 8.4 Hz).

Ethyl 4-[(7,8-dihydro-8,8-dimethyl-5-(2-thiazolyl)naphth-3-yl)ethynyl]benzoate (Compound 67)

A solution of 2-lithiothiazole was prepared by the addition of 41.2 mg (0.42 ml, 0.63 mmol) of n-butyllithium (1.5M solution in hexanes) to a cold solution (−78° C.) of 53.4 mg (0.63 mmol) of thiazole in 1.0 ml of THF. The solution was stirred at for 30 minutes and then a solution of 113.9 mg (0.84 mmol) of zinc chloride in 1.5 ml of THF was added. The resulting solution was warmed to room temperature, stirred for 30 minutes and then the organozinc was added via cannula to a solution of 200.0 mg (0.42 mmol) of ethyl 4-[(8-trifluoromethylsulfonyloxy-7,8-dihydro-8,8-dimethylnaphth-3-yl)ethynyl]benzoate (Compound 66) and 12.4 mg (0.01 mmol) of tetrakis(triphenylphosphine)palladium(0) in 1.5 ml of THF. The resulting solution was heated at 50° C. for 45 minutes, cooled to room temperature and diluted with sat. aqueous NH₄Cl. The mixture was extracted with EtOAc (40 ml) and the combined organic layers were washed with water and brine. The organic phase was dried over Na₂SO₄ and concentrated in vacuo to a yellow oil. Purification by column chromatography (silica, 20% EtOAc-hexanes) yielded the title compound as a colorless oil.

PMR (CDCl₃): δ1.35 (6H, s), 1.40 (3H, t, J=7.1 Hz), 2.42 (2H, d, J=4.8 Hz), 4.38 (2H, q, J=7.1 Hz), 6.57 (1H, t, J=4.8 Hz), 7.33 (1H, d, J=3.3 Hz), 7.36 (1H, d, J=8.0 Hz), 7.46 (1H, dd, J=1.7, 8.1 Hz), 7.55 (2H, d, J=8.4 Hz), 7.87 (1H, d, J=1.7 Hz), 7.92 (1H, d, J=3.3 Hz), 8.00 (2H, d, J=8.4 Hz).

Ethyl 4-[(7,8-dihydro-8,8-dimethyl-5-phenylnaphth-3-yl)ethynyl]benzoate (Compound 68)

Employing the same general procedure as for the preparation of ethyl 4-[(7,8-dihydro-8,8-dimethyl-5-(2-thiazolyl)naphth-3-yl)ethynyl]benzoate (Compound 67), 203.8 mg (0.43 mmol) of ethyl 4-[(5-trifluoromethylsulfonyloxy-7,8-dihydro-8,8-dimethylnaphth-3-yl)ethynyl]benzoate (Compound 66) was converted into the title compound (colorless solid) using 58.2 mg (0.36 ml, 0.69 mmol) of phenyllithium (1.8M solution in cyclohexane/Et₂O), 116.1 mg (0.85 mmol) of zinc chloride and 13.8 mg (0.01 mmol) of tetrakis(triphenylphosphine)palladium(0).

PMR (CDCl₃): δ1.36 (6H, s), 1.40 (3H, t, J=7.1 Hz), 2.37 (2H, d, J=4.7 Hz), 4.38 (2H, q, J=7.1 Hz), 6.02 (1H, t, J=4.7 Hz), 7.20 (1H, d, J=1.5 Hz), 7.27 (1H, m), 7.39 (6H, m), 7.52 (2H, d, J=8.2 Hz), 7.98 (2H, d, J=8.2 Hz).

Ethyl 4-[(7,8-dihydro-8,8-dimethyl-5-(4-(1,1-dimethylethyl)phenyl)naphth-3-yl)ethynyl]benzoate (Compound 69)

Employing the same general procedure as for the preparation of ethyl 4-[(7,8-dihydro-8,8-dimethyl-5-(2-thiazolyl)naphth-3-yl)ethynyl]benzoate (Compound 67), 250.0 mg (0.52 mmol) of ethyl 4-[(5-trifluoromethylsulfonyloxy-7,8-dihydro-8,8-dimethylnaphth-3-yl)ethynyl]benzoate (Compound 66) was converted into the title compound (colorless solid) using 142.4 mg (1.045 mmol) of zinc chloride, 24.1 mg (0.02 mmol) of tetrakis(triphenylphosphine)palladium(0) and 4-tert-butylphenyllithium (prepared by adding 100.6 mg (0.97 mL, 1.57 mmol) of tert-butyllithium (1.5M solution in pentane) to a cold solution (−78° C.) of 167.0 mg (0.78 mmol) of 4-tert-butylbromobenzene in 1.0 mL of THF).

PMR (CDCl₃): δ1.35 (6H, s), 1.39 (9H, s), 1.40 (3H, t, J=7.2 Hz), 1.59 (3H, s), 2.36 (2H, d, J=4.9 Hz), 4.38 (2H, q, J=7.2 Hz), 6.02 (1H, t, J=4.9 Hz), 7.28–7.45 (7H, m), 7.55 (2H, d, J=8.4 Hz), 7.99 (2H, d, J=8.4 Hz).

Ethyl 4-[(7,8-dihydro-8,8-dimethyl-5-(2-pyridyl)naphth-3-yl)ethynyl]benzoate (Compound 70)

Employing the same general procedure as for the preparation of ethyl 4-[(7,8-dihydro-8,8-dimethyl-5-(2-thiazolyl)naphth-2-yl)ethynyl]benzoate (Compound 67), 250.0 mg (0.52 mmol) of ethyl 4-[(5-trifluoromethylsulfonyloxy-7,8-dihydro-8,8-dimethylnaphth-3-yl)ethynyl]benzoate (Compound 66) was converted into the title compound (colorless solid) using 142.4 mg (1.045 mmol) of zinc chloride, 24.1 mg (0.02 mmol) of tetrakis(triphenylphosphine)palladium(0) and 2-lithiopyridine (prepared by the addition of 100.6 mg (0.97 ml, 1.57 mmol) of tert-butyllithium (1.5M solution in pentane) to a cold solution (−78° C.) of 123.8 mg (0.784 mmol) of 2-bromopyridine in 1.0 mL of THF).

PMR (d₆-acetone): δ1.35 (6H, s), 1.35 (3H, t, J=7.1 Hz), 2.42 (2H, d, J=4.7 Hz), 4.34 (2H, q, J=7.1 Hz), 6.32 (1H, t, J=4.7 Hz), 7.35 (2H, m), 7.47 (2H, d, J=1.1 Hz), 7.50 (1H, d, J=7.7 Hz), 7.58 (2H, d, J=8.4 Hz), 7.85 (1H, ddd, J=1.8, 7.7, 9.5 Hz), 7.99 (2H, d, J=8.4 Hz), 8.64 (1H, m).

Ethyl 4-[(7,8-dihydro-8,8-dimethyl-5-(1,1-dimethylethyl)naphth-3-yl)ethynyl]benzoate (Compound 71) and Ethyl 4-[(7,8-dihydro-8,8-dimethylnaphth-3-yl)ethynyl]benzoate (Compound 72)

A mixture of 35.1 mg (0.39 mmol) of cuprous cyanide and 16.6 mg (0.39 mmol) of lithium chloride was flame dried under vacuum, cooled to room temperature and dissolved in 1.5 ml of THF. This solution was cooled to −78° C. and 50.2 mg (0.46 mL, 0.784 mmol) of tert-butyllithium (1.7M solution in pentane) was added forming a clear yellow solution. The reaction mixture was stirred at −78° C. for 15 minutes and then 125.0 mg (0.26 mmol) of ethyl 4-[(5-trifluoromethylsulfonyloxy-7,8-dihydro-8,8-dimethylnaphth-3-yl)ethynyl]benzoate (Compound 66) was added as a solution in 0.5 ml of THF. After 10 minutes the reaction was quenched at −78° C. with 1.5 ml of a 2:1 (v/v) mixture of sat. aqueous NH₄Cl and 5% NaOH. The mixture was extracted with EtOAc and the combined organic layers were washed with water and brine. The organic phase was dried over MgSO₄, concentrated in vacuo and purified by column chromatography (silica, 5% EtOAc-hexanes) to give a clear yellow oil (7:5 ratio of title compounds). The two compounds were separated by HPLC (partisil 10, 2% EtOAc-hexanes) to give the title compounds as colorless oils.

Ethyl 4-[(7,8-dihydro-8,8-dimethyl-5-(1,1-dimethylethyl)naphth-3-yl)ethynyl]benzoate (Compound 71)

PMR (CDCl₃): δ1.23 (6H, s), 1.39 (9H, s), 1.42 (3H, t J=7.2 Hz), 2.16 (2H, d, J=4.9 Hz), 4.40 (2H, q, J=7.2 Hz), 6.01 (1H, t, J=4.9 Hz), 7.34 (2H, m, J=1.6, 7.3 Hz), 7.61 (2H, d, J=8.2 Hz), 7.81 (1H, d, J=1.6 Hz), 8.03 (2H, d, J=8.2 Hz).

Ethyl 4-[(7,8-dihydro-8,8-dimethylnaphth-3-yl)ethynyl]benzoate (Compound 72)

PMR (CDCl₃): δ1.28 (6H, s), 1.43 (3H, t, J=7.2 Hz), 2.27 (2H, dd, J=1.9, 4.4 Hz), 4.39 (2H, q, J=7.2 Hz), 5.99 (1H, dt,

J=4.4, 9.3 Hz), 6.44 (1H, dt, J=1.9, 9.3 Hz), 7.22 (1H, d, J=1.3 Hz), 7.26–7.39 (2H, m), 7.57 (2H, d, J=8.4 Hz), 8.02 (2H, d, J=8.2 Hz).

Ethyl 4-[(7,8-dihydro-5,8,8-trimethylnaphth-3-yl)ethynyl]benzoate (Compound 73)

Employing the same general procedure as for the preparation of ethyl 4-(7,8-dihydro-8,8-dimethyl-5-(1,1-dimethylethyl)naphth-3-yl)ethynyl]benzoate (Compound 71), 250 mg (0.52 mmol) of ethyl 4-[(5-trifluoromethylsulfonyloxy-7,8-dihydro-8,8-dimethylnaphth-3-yl)ethynyl]benzoate (Compound 66) was converted into the title compound (HPLC Partisil 10, 0.5% EtOAC-hexanes) using 70.2 mg (0.78 mmol) of cuprous cyanide, 33.2 mg (0.78 mmol) of lithium chloride and 34.5 mg (1.28 ml, 1.57 mmol) of methyllithium (1.22M solution in $Et_2O$).

PMR ($CDCl_3$): δ1.27 (6H, s), 1.41 (3H, t, J=7.1 Hz), 2.09 (3H, d, J=1.7 Hz), 2.21 (2H, dd, J=1.8, 4.1 Hz), 4.39 (2H, q, J=7.1 Hz), 5.82 (1H, br m), 7.30 (1H, d, J=7.7 Hz), 7.40 (2H, d, J=8.3 Hz), 7.60 (2H, d, J=7.3 Hz), 8.03 (2H, d, J=8.3 Hz).

4-[(5-butyl-7,8-dihydro-8,8-dimethylnaphth-3-yl)ethynyl]benzoate (Compound 74)

Employing the same general procedure as for the preparation of ethyl 4-[(7,8-dihydro-8,8-dimethyl-5-(1,1-dimethylethyl)naphth-3-yl)ethynyl]benzoate (Compound 71), 98.1 mg (0.205 mmol) of ethyl 4-[(5-trifluoromethylsulfonyloxy-7,8-dihydro-8,8-dimethylnaphth-3-yl)ethynyl]benzoate (Compound 66) was converted into the title compound (HPLC Partisil 10, 1% tBuOMe-hexanes) using a mixture of 27.5 mg (0.31 mmol) of cuprous cyanide and 13.0 mg (0.31 mmol) of lithium chloride in 1.5 ml of $Et_2O$ treated with 39.4 mg (0.41 ml, 0.62 mmol) of n-butyllithium (1.5M solution in hexane).

PMR ($CDCl_3$): δ0.96 (3H, t), 1.26 (6H, s), 1.42 (3H, t, J=7.1 Hz), 1.43 (2H, m), 1.55 (2H, m), 2.20 (2H, d, J=4.5 Hz), 2.47 (2H, t, J=6.5 Hz), 4.39 (2H, q, J=7.1 Hz), 5.80 (1H, t, J=4.5 Hz), 7.31 (1H, d, J=8.0 Hz), 7.39 (1H, dd, J=1.8, 8.0 Hz), 7.43 (1H, br s), 7.61 (2H, d, J=8.2 Hz), 8.03 (2H, d, J=8.2 Hz).

Ethyl 4-[(7,8-dihydro-8,8-dimethyl-5-(1-pentynyl)naphth-3-yl)ethynyl]benzoate (Compound 75)

A solution (flushed with argon) of 201.3 mg (0.42 mmol) of ethyl 4-[(5-trifluoromethylsulfonyloxy-7,8-dihydro-8,8-dimethylnaphth-3-yl)ethynyl]benzoate (Compound 66), 286.5 mg (4.21 mmol) of 1-pentyne, 59.5 mg (0.08 mmol) of bis(triphenylphosphine)palladium(II) chloride and 32.0 mg (0.17 mmol) of cuprous iodide in 2.5 ml of diethylamine was heated to 70° C. in a pressure vial for 6 hours. After stirring overnight at room temperature, the mixture was diluted with EtOAc (25 ml) and washed with water and brine. The organic phase was dried over $MgSO_4$, concentrated in vacuo and purified by column chromatography (silica, 5% $Et_2O$-hexanes) to give the title compound as a colorless, air-sensitive oil.

PMR ($CDCl_3$): δ1.10 (3H, t, J=7.2 Hz), 1.28 (6H, s), 1.42 (3H, t, J=7.2 Hz), 1.69 (2H, sextet, J=7.2 Hz), 2.31 (2H, d, J=4.7 Hz), 2.46 (2H, t, J=7.0 Hz), 4.39 (2H, q, J=7.2 Hz), 6.35 (1H, t, J=4.7 Hz), 7.30 (1H, s), 7.42 (1H, dd, J=1.5, 7.8 Hz), 7.59 (2H, d, J=8.3 Hz), 7.82 (1H, d, J=1.5 Hz), 8.03 (2H, d, J=8.3 Hz).

Ethyl 4-[(7,8-dihydro-8,8-dimethyl-5-(1-(3,3-dimethyl)butynyl)naphth-3-yl)ethynyl]benzoate (Compound 76)

Employing the same general procedure as for the preparation of ethyl 4-[(7,8-dihydro-8,8-dimethyl-5-(1-pentynyl) naphth-3-yl)ethynyl]benzoate (Compound 75), 184.3 mg (0.39 mmol) of ethyl 4-[(5-trifluoromethylsulfonyloxy-7,8-dihydro-8,8-dimethylnaphth-3-yl)ethynyl]benzoate (Compound 66) was converted into the title compound (pale yellow oil) using 316.4 mg (3.85 mmol) 3,3-dimethyl-1-butyne, 54.5 mg (0.08 mmol) of bis(triphenylphosphine) palladium(II) chloride and 29.3 mg (0.15 mmol) of cuprous iodide.

PMR ($CDCl_3$): δ1.28 (6H, s), 1.39 (9H, s), 1.41 (3H, t, J=7.2 Hz) 2.31 (2H, d, J=4.9 Hz), 4.39 (2H, q, J=7.2 Hz), 6.33 (1H, t, J=4.9 Hz), 7.29 (1H, s), 7.41 (1H, dd, J=1.7, 8.0 Hz), 7.59 (2H, d, J=8.4 Hz), 7.76 (1H, d, J=1.7 Hz), 8.03 (2H, d, J=8.4 Hz).

Ethyl 4-[(7,8-dihydro-8,8-dimethyl-5-(1-propynyl)naphth-3-yl)ethynyl]benzoate (Compound 77)

Into a solution of 263.7 mg (0.55 mmol) of ethyl 4-[(5-trifluoromethylsulfonyloxy-7,8-dihydro-8,8-dimethylnaphth-3-yl)ethynyl]benzoate (Compound 66), 4.2 mg (0.02 mmol) cuprous iodide and 7.8 mg (0.11 mmol) bis(triphenylphosphine)palladium(II) chloride in 2.0 ml of DMF and 1.0 ml of diethylamine was bubbled propyne. The initial blue solution turned brown in color after 45 minutes of stirring at room temperature. The reaction mixture was diluted with EtOAc (40 ml) and washed with water and brine. The organic phase was dried over $MgSO_4$, concentrated in vacuo and purified by column chromatography (silica, 5% $Et_2O$-hexanes) to give the title compound as a colorless solid.

PMR ($CDCl_3$): δ1.38 (6H, s), 1.42 (3H, t, J=7.2 Hz), 2.12 (3H, s), 2.31 (2H, d, J=4.8 Hz), 4.40 (2H, q, J=7.2 Hz), 6.34 (1H, t, J=4.8 Hz), 7.30 (1H, s), 7.42 (1H, dd, J=1.5, 7.6 Hz), 7.61 (2H, d, J=8.6 Hz) 7.78 (1H, d, J=1.5 Hz), 8.03 (2H, d, J=8.6 Hz).

4-[(7,8-dihydro-8,8-dimethyl-5-(2-thiazolyl)naphth-3-yl)ethynyl]benzoic acid (Compound 78)

A solution of 33.9 mg (0.08 mmol) of ethyl 4-[(7,8-dihydro-8,8-dimethyl-5-(2-thiazolyl)naphth-3-yl)ethynyl] benzoate (Compound 67) and 8.5 mg (0.20 mmol) of $LiOH-H_2O$ in 3 ml of THF/water (3:1, v/v), was stirred overnight at room temperature. The reaction was quenched by the addition of sat. aqueous $NH_4Cl$ and extracted with EtOAc. The combined organic layers were washed with water and brine, dried over $Na_2SO_4$ and concentrated in vacuo to give the title compound as a colorless solid.

PMR ($d_6$-DMSO): δ1.29 (6H, s), 2.42 (2H, d, J=4.6 Hz), 6.68 (1H, t, J=4.6 Hz), 7.51 (2H, m), 7.62 (2H, d, J=8.2 Hz), 7.77 (1H, d, J=3.3 Hz), 7.93 (2H, d, J=8.2 Hz), 7.98 (1H, d, J=3.3 Hz).

4-[(7,8-dihydro-8,8-dimethyl-5-phenylnaphth-2-yl)ethynyl]benzoic acid (Compound 79)

Employing the same general procedure as for the preparation of 4-[(7,8-dihydro-8,8-dimethyl-5-(2-thiazolyl)naphth-3-yl)ethynyl]benzoic acid (Compound 78), 27.0 mg (0.07 mmol) of ethyl 4-[(7,8-dihydro-8,8-dimethyl-5-phenylnaphth-3-yl)ethynyl]benzoate (Compound 68) was converted into the title compound (colorless solid) using 5.9 mg (0.14 mmol) of LiOH in $H_2O$.

PMR ($d_6$-DMSO): δ1.31 (6H, s), 2.35 (2H, d, J=4.5 Hz), 6.05 (1H, t, J=4.5 Hz), 7.00 (1H, s), 7.33 (2H, d, J=6.2 Hz), 7.44 (4H, m), 7.59 (2H, d, J=8.1 Hz), 7.90 (2H, d, J=8.1 Hz).

4-[(7,8-dihydro-8,8-dimethyl-5-(1,1-dimethylethyl)naphth-3-yl)ethynyl]benzoic acid (Compound 80)

A solution of 24.0 mg (0.06 mmol) of ethyl 4-[(7,8-dihydro-8,8-dimethyl-5-(1,1-dimethylethyl)naphth-3-yl)

ethynyl]benzoate (Compound 71) and 6.5 mg (0.16 mmol) of LiOH—H$_2$O in 3 mL THF/water (3:1, v/v) was stirred overnight (22 hours) at room temperature. The reaction mixture was extracted with Et$_2$O and the layers were separated. The aqueous layer was acidified with HCl (1M aqueous solution) and then extracted with EtOAc. The organic phase was dried over Na$_2$SO$_4$ and concentrated in vacuo to give the title compound as a colorless solid.

PMR (d$_6$-DMSO): δ1.23 (6H, s), 1.37 (9H, s), 2.16 (2H, d, J=4.9 q 1 Hz), 6.07 (1H, t, J=4.9 Hz), 7.40 (2H, s), 7.66 (2H, d, J=8.1 Hz), 7.84 (1H,s), 8.06 (2H, d, J=8.1 Hz).

4-[(7,8-dihydro-8,8-dimethylnaphth-3-yl)ethynyl]benzoic acid (Compound 81)

Employing the same general procedure as for the preparation of 4-[(7,8-dihydro-8,8-dimethyl-5-(1,1-dimethylethyl)naphth-3-yl)ethynyl]benzoic acid (Compound 80), 25.3 mg (0.08 mmol) of ethyl 4-[(7,8-dihydro-8,8-dimethylnaphth-3-yl)ethynyl]benzoate (Compound 72) was converted into the title compound (colorless solid) using 8.0 mg (0.14 mmol) of LiOH in H$_2$O.

PMR (d$_6$-DMSO): δ1.26 (6H, s), 2.27 (2H, dd, J=2.9, 4.4 Hz), 6.03 (1H, dt, J=4.4, 9.6 Hz), 6.51 (1H, ddd, J=1.9, 3.6, 9.6 Hz), 7.27 (1H, s), 7.39 (2H, m), 7.67 (2H, d, J=7.6 Hz), 8.07 (2H, J=7.6 Hz).

4-[(5,8,8-trimethyl-7,8-dihydronaphth-3-yl)ethynyl]benzoic acid (Compound 82)

Employing the same general procedure as for the preparation of 4-[(7,8-dihydro-8,8-dimethyl-5-(1,1-dimethylethyl)naphth-3-yl)ethynyl]benzoic acid (Compound 80), 33.7 mg (0.10 mmol) of ethyl 4-[(7,8-dihydro-5,8,8-trimethylnaphth-3-yl)ethynyl]benzoate (Compound 73) was converted into the title compound (colorless solid) using 10.2 mg (0.25 mmol) of LiOH in H$_2$O.

PMR (d$_6$-DMSO): δ1.22 (6H, s), 2.06 (3H, d, J=1.4 Hz), 2.18 (2H, dd, J=2.1, 4.5 Hz), 5.87 (1H, br m), 7.42 (3H, m), 7.67 (2H, d, J=8.4 Hz), 7.97 (2H, d, J=8.4 Hz).

4-[(5-butyl-8,8-dimethyl-7,8-dihydronaphth-3-yl)ethynyl]benzoic acid (Compound 83)

Employing the same general procedure as for the preparation of 4-[(7,8-dihydro-8,8-dimethyl-5-(1,1-dimethylethyl)naphth-3-yl)ethynyl]benzoic acid (Compound 80), 22.6 mg (0.06 mmol) of ethyl 4-[(5-butyl-7,8-dihydro-8,8-dimethylnaphth-3-yl)-ethynyl]benzoate (Compound 74) was converted into the title compound using 6.1 mg (0.146 mmol) of LiOH in H$_2$O.

PMR (d$_6$-DMSO): δ0.90 (3H, t, J=7.1 Hz), 1.20 (6H, s), 1.35 (2H, m), 1.45 (2H, m), 2.16 (2H, d, J=4.2 Hz), 2.43 (2H, t), 5.82 (1H, d, J=4.2 Hz), 7.36 (1H, m), 7.43 (2H, d), 7.84 (2H, d).

4-[(7,8-dihydro-8,8-dimethyl-5-(1-pentynyl)naphth-3-yl)ethynyl]benzoic acid (Compound 84)

Employing the same general procedure as for the preparation of 4-[(7,8-dihydro-8,8-dimethyl-5-(1,1-dimethylethyl)naphth-3-yl)ethynyl]benzoic acid (Compound 80), 42.0 mg (0.106 mmol) of ethyl 4-[(7,8-dihydro-8,8-dimethyl-5-(1-pentynyl)naphth-3-yl)ethynyl]benzoate (Compound 75) was converted into the title compound (colorless solid) using 11.1 mg (0.27 mmol) of LiOH in H$_2$O in 3 mL of THF/water (3:1, v/v, flushed with argon).

PMR (d$_6$-DMSO): δ1.04 (3H, br t), 1.22 (6H,s), 1.59 (2H, m), 2.30 (2H, m), 2.45 (2H, m), 6.37 (1H, br t), 7.38 (1H, m), 7.48 (1H, m), 7.60 (2H, d, J=7.4 Hz), 7.67 (1H, s), 7.96 2H, d, J=7.4 Hz).

4-[(7,8-dihydro-8,8-dimethyl-5-(1-(3,3-dimethyl)butynyl)naphth-3-yl)ethynyl]benzoic acid (Compound 85)

Employing the same general procedure as for the preparation of 4-((7,8-dihydro-8,8-dimethyl-5-(1-pentynyl)naphth-3-yl)ethynyl]benzoic acid (Compound 84), 34.7 mg (0.085 mmol) of ethyl 4-[(7,8-dihydro-8,8-dimethyl-5-(1-(3, 3-dimethyl)butynyl)naphth-3-yl)ethynyl]benzoate (Compound 76) was converted into the title compound (colorless solid) using 9.6 mg (0.23 mmol) of LiOH in H$_2$O.

PMR (d$_6$-DMSO): δ1.21 (6H, s), 1.32 (9H, s), 2.29 (2H, d, J=4.8 Hz), 6.34 (1H, t, J=4.8 Hz), 7.39 (1H, d, J=8.0 Hz), 7.48 (1H, dd, J=1.8, 8.0 Hz), 7.61 (1H, d, J=1.8 Hz), 7.65 (2H, d, J=8.3 Hz), 7.96 (2H, d, J=8.3 Hz).

4-[(7,8-dihydro-8,8-dimethyl-5-(1-propynyl)naphth-3-yl)ethynyl]benzoic acid (Compound 86)

Employing the same general procedure as for the preparation of 4-[(7,8-dihydro-8,8-dimethyl-5-(1-pentynyl)naphth-3-yl)ethynyl]benzoic acid (Compound 84), 75.0 mg (0.204 mmol) of ethyl 4-[(7,8-dihydro-8,8-dimethyl-5-(1-propynyl)naphth-3-yl)ethynyl]benzoate (Compound 77) was converted into the title compound (colorless solid) using 21.4 mg (0.51 mmol) of LiOH in H$_2$O.

PMR (d$_6$-DMSO): δ1.22 (6H, s), 2.10 (3H, s), 2.30 (2H, d, J=4.5 Hz), 6.38 (1H, t, J=4.5 Hz), 7.39 (2H, d, J=8.2 Hz), 7.47 (2H, d, J=7.7 Hz), 7.54 (2H, d, J=7.7 Hz), 7.61 (1H, s), 7.89 (2H, d, J=7.7 Hz).

Ethyl 4-[(5-trifluoromethylsulfonyloxy-7,8-dihydro-8,8-dimethylnaphth-2-yl)ethynyl]benzoate (Compound 87)

Employing the same general procedure as for the preparation of ethyl 4-[(5-trifluoromethylsulfonyloxy-7,8-dihydro-8,8-dimethylnaphth-3-yl)ethynyl]benzoate (Compound 66), 800 mg (2.31 mmol) of ethyl 4-[(5,6,7,8-tetrahydro-8,8-dimethyl-5-oxonaphth-2-yl)ethynyl]benzoate (Compound 1) in 2 ml of THF was converted into the title compound (white solid) using 466 mg (2.5 ml, 2.54 mmol) of sodium bis(trimethylsilyl)amide (1.0M solution in THF) and a solution of 961 mg (2.54 mmol) of 2-[N,N-bis(trifluoromethylsulfonyloxy)amino]-5-chloropyridine in 2 ml of THF.

PMR (CDCl$_3$): δ1.34 (6H, s), 1.41 (3H, t, J=7.2 Hz), 2.44 (2H, d, J=4.8 Hz), 4.39 (2H, q, J=7.2 Hz), 6.01 (1H, t, J=4.8 Hz), 7.37 (1H, d, J=8.0 Hz), 7.45 (1H, dd, J=1.5, 8.0 Hz), 7.48 (1H, d, J=1.5 Hz), 7.60 (2H, d, J=8.3 Hz), 8.04 (2H, d, J=8.3 Hz).

Ethyl 4-[(7,8-dihydro-8,8-dimethyl-5-(2-thiazolyl)naphth-2-yl)ethynyl]benzoate (Compound 88)

Employing the same general procedure as for the preparation of ethyl 4-[(7,8-dihydro-8,8-dimethyl-5-(2-thiazolyl)naphth-3-yl)ethynyl]benzoate (Compound 67),400 mg (0.84 mmol) of ethyl 4-[(5-trifluoromethylsulfonyloxy-7,8-dihydro-8,8-dimethylnaphth-2-yl)ethynyl]benzoate (Compound 87) in 2 ml of THF was converted into the title compound (white solid) using a solution of 82 mg (1.26 mmol) of thiazole in 2 ml of THF, 81 mg (0.84 ml, 1.26 mmol) of n-butyllithium (1.5M solution in hexanes), 228 mg (3.36 ml, 1.68 mmol) of zinc chloride (0.5M solution in THF) and 10 mg (0.01 mmol) of tetrakis(triphenylphosphine)palladium (0).

PMR (CDCl$_3$): δ1.36 (6H, s), 1.41 (3H, t, J=7.2 Hz), 2.42 (2H, d, J=4.9 Hz), 4.39 (2H, q, J=7.2 Hz), 6.58 (1H, t, J=4.9

Hz), 7.32 (1H, d, J=3.4 Hz), 7.38 (1H, dd, J=1.7, 8.1 Hz), 7.54 (1H, d, J=1.7 Hz), 7.60 (2H, d, J=8.2 Hz), 7.72 (1H, d, J=8.1 Hz), 7.87 (1H, d, J=3.4 Hz), 8.02 (2H, d, J=8.2 Hz).

Ethyl 4-[(7,8-dihydro-8,8-dimethyl-5-phenylnaphth-2-yl)ethynyl]benzoate (Compound 89)

Employing the same general procedure as for the preparation of ethyl 4-[(7,8-dihydro-8,8-dimethyl-5-(2-thiazolyl)naphth-3-yl)ethynyl]benzoate (Compound 67), 200 mg (0.42 mmol) of ethyl 4-[(5-trifluoromethylsulfonyloxy)-7,8-dihydro-8,8-dimethylnaphth-2-yl)ethynyl]benzoate (Compound 87) in 1 ml of THF was converted into the title compound (white solid) using 53 mg (0.35 ml, 0.63 mmol) of phenyllithium (1.8M in cyclohexane/Et$_2$O), 81 mg (0.84 ml, 1.26 mmol) of n-butyllithium (1.5M solution in hexanes), 86 mg (1.26 ml, 0.63 mmol) of zinc chloride (0.5M solution in THF) and 10 mg (0.01 mmol) of tetrakis(triphenylphosphine)palladium (0).

PMR (CDCl$_3$): δ1.36 (6H, s), 1.40 (3H, t, J=7.2 Hz), 2.37 (2H, d, J=4.9 Hz), 4.38 (2H, q, J=7.2 Hz), 6.03 (1H, t, J=4.9 Hz), 7.01 (1H, d, J=8.0 Hz), 7.27 (1H, dd, J=1.7, 8.0 Hz), 7.31–7.41 (5H, m), 7.53 (1H, d, J=1.7 Hz), 7.59 (2H, d, J=8.2 Hz), 8.02 (2H, d, J=8.2 Hz).

Ethyl 4-[(7,8-dihydro-8,8-dimethyl-5-(phenylethyn-1-yl)naphth-2-yl)ethynyl]benzoate (Compound 90)

Employing the same general procedure as for the preparation of ethyl 4-[(7,8-dihydro-8,8-dimethyl-5-(1-pentynyl)naphth-3-yl)ethynyl]benzoate (Compound 75), 200 mg (0.42 mmol) of ethyl 4-[(5-trifluoromethylsulfonyloxy-7,8-dihydro-8,8 -dimethylnaphth-2-yl)ethynyl]benzoate (Compound 87) was converted into the title compound (pale yellow oil) using 429 mg (4.2 mmol) of phenylacetylene, 60 mg (0.08 mmol) of bis(triphenylphosphine)palladium (II) chloride and 20 mg (0.11 mmol) of cuprous iodide.

PMR (CDCl$_3$): δ1.32 (6H, s), 1.40 (3H, t, J=7.1 Hz), 2.38 (2H, d, J=5.0 Hz), 4.38 (2H, q, J=7.1 Hz), 6.53 (1H, t, J=5.0 Hz), 7.32–7.38 (3H, m), 7.43 (1H, dd, J=1.6, 7.9 Hz), 7.50 (1H, d, J=1.6 Hz), 7.54 (1H, d, J=1.6 Hz), 7.56 (1H, d, J=4.8), 7.61 (2H, d, J=8.2 Hz), 7.70 (1H, d, J=7.9 Hz), 8.03 (2H, d, J=8.2 Hz).

Ethyl 4-[(7,8-dihydro-8,8-dimethyl-5-(1-(3-hydroxy-3-methyl)butynyl)naphth-2-yl)ethynyl]benzoate (Compound 91)

Employing the same general procedure as for the preparation of ethyl 4-[(7,8-dihydro-8,8-dimethyl-5-(1-pentynyl)naphth-3-yl)ethynyl]benzoate (Compound 75), 200 mg (0.42 mmol) of ethyl 4-[(5-trifluoromethylsulfonyloxy-7,8-dihydro-8,8-dimethylnaphth-2-yl)ethynyl]benzoate (Compound 87) was converted into the title compound (pale yellow solid) using 353 mg (4.2 mmol) of 2-methyl-3-butyn-2-ol, 60 mg (0.08 mmol) of bis(triphenylphosphine)palladium (II) chloride and 20 mg (0.11 mmol) of cuprous iodide.

PMR (CDCl$_3$): δ1.28 (6H, s), 1.40 (3H, t, J=7.1 Hz), 1.65 (6H, s), 2.31 (2H, d, J=4.8 Hz), 4.38 (2H, q, J=7.1 Hz), 6.39 (1H, t, J=4.8 Hz), 7.38 (1H, dd, J=1.6, 7.9 Hz), 7.46 (1H, d, J=1.6 Hz), 7.56 (1H, d, J=7.9 Hz), 7.58 (2H, d, J=8.2 Hz), 8.02 (2H, d, J=8.2 Hz).

Ethyl 4-[(7,8-dihydro-8,8-dimethyl-5-(1-propynyl)naphth-2-yl)ethynyl]benzoate (Compound 92)

Employing the same general procedure as for the preparation of ethyl 4-[(7,8-dihydro-8,8-dimethyl-5-(1-pentynyl)naphth-3-yl)ethynyl]benzoate (Compound 75), 200 mg (0.42 mmol) of ethyl 4-[(5-trifluoromethylsulfonyloxy-7,8-dihydro-8,8-dimethylnaphth-2-yl)ethynyl]benzoate (Compound 87) was converted into the title compound (pale yellow oil) using 168 mg (4.2 mmol) of propyne, 60 mg (0.08 mmol) of bis(triphenylphosphine)palladium (II) chloride and 20 mg (0.11 mmol) of cuprous iodide.

PMR (CDCl$_3$): δ1.28 (6H, s), 1.40 (3H, t, J=7.1 Hz), 2.08 (3H, s), 2.30 (2H, d, J=4.8 Hz), 4.38 (2H, q, J=7.1 Hz), 6.33 (1H, t, J=4.8 Hz), 7.40 (1H, dd, J=1.6, 7.9 Hz), 7.45 (1H, d, J=1.6 Hz), 7.59 (1H, d, J=7.9 Hz), 7.61 (2H, d, J=8.2 Hz), 8.02 (2H, d, J=8.2 Hz).

Ethyl 4-[(7,8-dihydro-8,8-dimethyl-5-(1-pentynyl)naphth-2-yl)ethynyl]benzoate (Compound 93)

Employing the same general procedure as for the preparation of ethyl 4-[(7,8-dihydro-8,8-dimethyl-5-(1-pentynyl)naphth-3-yl)ethynyl]benzoate (Compound 75), 200 mg (0.42 mmol) of ethyl 4-[(5-trifluoromethylsulfonyloxy-7,8-dihydro-8,8-dimethylnaphth-2-yl)ethynyl]benzoate (Compound 87) was converted into the title compound (pale yellow oil) using 286 mg (4.2 mmol) of pentyne, 60 mg (0.08 mmol) of bis(triphenylphosphine)palladium (II) chloride and 20 mg (0.11 mmol) of cuprous iodide.

PMR (CDCl$_3$): δ1.06 (3H, t, J=7.3 Hz), 1.28 (6H, s), 1.39 (3H, t, J=7.1 Hz), 1.65 (2H, sext, J=7.3 Hz), 2.30 (2H, d, J=4.8 Hz), 2.41 (2H, t, J=7.3 Hz), 4.37 (2H, q, J=7.1 Hz), 6.34 (1H, t, J=4.8 Hz), 7.40 (1H, dd, J=1.6, 7.9 Hz), 7.45 (1H, d, J=1.6 Hz), 7.59 (2H, d, J=8.1 Hz), 7.62 (1H, d, J=7.9 Hz), 8.01 (2H, d, J=8.1 Hz).

Ethyl 4-[(7,8-dihydro-8,8-dimethyl-5-(1-(3,3-dimethyl)butynyl)naphth-2-yl)ethynyl]benzoate (Compound 94)

Employing the same general procedure as for the preparation of ethyl 4-[(7,8-dihydro-8,8-dimethyl-5-(1-pentynyl)naphth-3-yl)ethynyl]benzoate (Compound 75), 200 mg (0.42 mmol) of ethyl 4-[(5-trifluoromethylsulfonyloxy-7,8-dihydro-8,8-dimethylnaphth-2-yl)ethynyl]benzoate (Compound 87) was converted into the title compound (pale yellow oil) using 70 mg (0.84 mmol) of 3,3-dimethyl-1-butyne, 60 mg (0.08 mmol) of bis(triphenylphosphine)palladium (II) chloride and 20 mg (0.11 mmol) of cuprous iodide.

PMR (CDCl$_3$): δ1.28 (6H, s), 1.35 (9H, s), 1.40 (3H, t, J=7.1 Hz), 2.29 (2H, d, J=4.8 Hz), 4.38 (2H, q, J=7.1 Hz), 6.32 (1H, t, J=4.8 Hz), 7.40 (1H, dd, J=1.6, 7.9 Hz), 7.45 (1H, d, J=1.6 Hz), 7.59 (3H, d, J=8.1 Hz), 8.01 (2H, d, J=8.1 Hz).

Ethyl 4-[(7,8-dihydro-5,8,8-trimethylnaphth-2-yl)ethynyl]benzoate (Compound 95)

Employing the same general procedure as for the preparation of ethyl 4-[(7,8-dihydro-8,8-dimethyl-5-(1,1-dimethylethyl)naphth-3-yl)ethynyl]benzoate (Compound 71), 300 mg (0.63 mmol) of ethyl 4-[(5-trifluoromethylsulfonyloxy-7,8-dihydro-8,8-dimethylnaphth-2-yl)ethynyl]benzoate (Compound 87) was converted into the title compound (colorless oil) using 84 mg (0.94 mmol) of cuprous cyanide, 40 mg (0.94 mmol) of lithium chloride and 41 mg (1.54 ml, 1.88 mmol) of methyllithium (1.22M solution in Et$_2$O).

PMR (CDCl$_3$): δ1.27 (6H, s), 1.40 (3H, t, J=7.1 Hz), 2.05 (3H, d, J=1.9 Hz), 2.21 (2H, dd, J=1.9, 4.8 Hz), 4.38 (2H, q, J=7.1 Hz), 5.81 (1H, dt, J=1.9, 4.8 Hz), 7.21 (1H, d J=8.0

Hz), 7.38 (1H, dd, J=1.6, 8.0 Hz), 7.47 (1H, d, J=1.6 Hz), 7.59 (2H, d, J=8.1 Hz), 8.02 (2H, d, J=8.1 Hz).

Ethyl 4-[(7,8-dihydro-8,8-dimethyl-5-(1,1-dimethylethyl)naphth-2-yl)ethynyl]benzoate (Compound 96)

Employing the same general procedure as for the preparation of ethyl 4-[(7,8-dihydro-8,8-dimethyl-5-(1,1-dimethylethyl)naphth-3-yl)ethynyl]benzoate (Compound 71), 300 mg (0.63 mmol) of ethyl 4-[(5-trifluoromethylsulfonyloxy-7,8-dihydro-8,8-dimethylnaphth-2-yl)ethynyl]benzoate (Compound 87) was converted into the title compound (colorless oil) using 84 mg (0.94 mmol) of cuprous cyanide, 40 mg (0.94 mmol) of lithium chloride and 120 mg (1.1 ml, 1.88 mmol) of tert-butyllithium (1.7M solution in pentane).

PMR (CDCl$_3$): δ1.24 (6H, s), 1.35 (9H, s), 1.40 (3H, t, J=7.1 Hz), 2.15 (2H, d, J=4.9 Hz), 4.38 (2H, q, J=7.1 Hz), 6.00 (1H, t, J=4.9 Hz), 7.34 (1H, dd J=2.0, 8.1 Hz), 7.48 (1H, d, J=2.0 Hz), 7.59 (2H, d, J=8.2 Hz), 7.63 (1H, d, J=8.1 Hz), 8.02 (2H, d, J=8.2 Hz).

4-[(7,8-dihydro-8,8-dimethyl-5-phenylnaphth-2-yl) ethynyl]benzoic acid (Compound 97)

To a solution of 50 mg (0.13 mmol) of ethyl 4-[(7,8-dihydro-8,8-dimethyl-5-phenylnaphth-2-yl)ethynyl] benzoate (Compound 89) in 1 ml of argon saturated THF was added 27 mg (1.3 ml, 0.65 mmol) of argon saturated LiOH (0.5M aqueous solution). The reaction mixture was stirred at room temperature for 24 hours under an atmosphere of argon, concentrated in vacuo and the resulting residue partitioned between water and hexanes. The layers were separated and the aqueous fraction was acidified to pH 1 with 2N HCl. The product was extracted into Et$_2$O, dried over MgSO$_4$, and concentrated in vacuo to give the title compound as a pale yellow solid.

PMR (DMSO-d$_6$): δ1.37 (6H, S), 2.38 (2H, d, J=4.7 Hz), 6.03 (1H, t, J=4.7 Hz), 6.99 (1H, d, J=8.1 Hz), 7.26 (1H, dd, J=1.7, 8.1 Hz), 7.30–7.42 (5H, m), 7.52 (1H, d, J=1.7 Hz), 7.58 (2H, d, J=8.2 Hz), 8.00 (2H, d, J=8.2 Hz).

4-[(7,8-dihydro-8,8-dimethyl-5-(phenylethyn-1-yl) naphth-2-yl)ethynyl]benzoic acid (Compound 98)

Employing the same general procedure as for the preparation of 4-[(7,8-dihydro-8,8-dimethyl-5-phenylnaphth-2-yl)ethynyl]benzoic acid (Compound 97), 22 mg (0.05 mmol) of ethyl 4-[(7,8-dihydro-8,8-dimethyl-5-(phenylethyn-1-yl)naphth-2-yl)ethynyl]benzoate (Compound 90) was converted to the title compound (pale yellow solid) using 11 mg (0.5 ml, 0.26 mmol) of LiOH (0.5 M aqueous solution).

PMR (CDCl$_3$): δ1.33 (6H, s), 2.40 (2H, d, J=4.9 Hz), 6.54 (1H, t, J=4.9 Hz), 7.33–7.40 (3H,m), 7.45 (1H, dd, J=1.6, 7.9 Hz), 7.51 (1H, d, J=1.6 Hz), 7.55 (1H, d, J=1.6 Hz), 7.57 (1H, d, J=4.8), 7.65 (2H, d, J=8.2 Hz), 7.72 (1H, d, J=7.9 Hz), 8.12 (2H, d, J=8.2 Hz).

4-[(7,8-dihydro-8,8-dimethyl-5-(1-(3-hydroxy-3-methyl)butynyl)naphth-2-yl)ethynyl]benzoic acid (Compound 99)

Employing the same general procedure as for the preparation of 4-[(7,8-dihydro-8,8-dimethyl-5-phenylnaphth-2-yl)ethynyl]benzoic acid (Compound 97), 79 mg (0.19 mmol) of ethyl 4-[(7,8-dihydro-8,8-dimethyl-5-(1-(3-hydroxy-3-methyl)butynyl)naphth-2-yl)ethynyl]benzoate (Compound 91) was converted to the title compound (pale yellow solid) using 40 mg (1.92 ml, 0.96 mmol) of LiOH (0.5 M aqueous solution).

PMR (acetone-d$_6$): δ1.29 (6H, s), 1.56 (6H, s), 2.35 (2H, d, J=5.1 Hz), 6.39 (1H, t, J=5.1 Hz), 7.45 (1H, dd, J=1.6, 7.9 Hz), 7.46 (1H, d, J=1.6 Hz), 7.64 (1H, d, J=7.9 Hz), 7.68 (2H, d, J=8.2 Hz), 8.06 (2H, d, J=8.2 Hz).

4-[(7,8-dihydro-8,8-dimethyl-5-(1-propynyl)naphth-2-yl)ethynyl]benzoic acid (Compound 100)

Employing the same general procedure as for the preparation of 4-[(7,8-dihydro-8,8-dimethyl-5-phenylnaphth-2-yl)ethynyl]benzoic acid (Compound 97), 75 mg (0.20 mmol) of ethyl 4-[(7,8-dihydro-8,8-dimethyl-5-(1-propynyl)naphth-2-yl)ethynyl]benzoate (Compound 92) was converted to the title compound (pale yellow solid) using 42 mg (2 ml, 1.0 mmol) of LiOH (0.5 M aqueous solution).

PMR (DMSO-d$_6$): δ1.21 (6H, s), 2.05 (3H, s), 2.28 (2H, d, J=4.7 Hz), 6.36 (1H, t, J=4.7 Hz), 7.46 (1H, dd, J=1.6, 7.9 Hz), 7.48 (1H, d, J=1.6 Hz), 7.55 (1H, d, J=7.9 Hz), 7.66 (2H, d, J=8.2 Hz), 7.96 (2H, d, J=8.2 Hz).

4-[(7,8-dihydro-8,8-dimethyl-5-(1-(3.3-dimethyl) butynyl)naphth-2-yl)ethynyl]benzoic acid (Compound 101)

Employing the same general procedure as for the preparation of 4-[(7,8-dihydro-8,8-dimethyl-5-phenylnaphth-2-yl)ethynyl]benzoic acid (Compound 97), 52 mg (0.13 mmol) of ethyl 4-[(7,8-dihydro-8,8-dimethyl-5-(1-(3,3-dimethyl)butynyl)naphth-2 -yl)ethynyl]benzoate (Compound 94) was converted to the title compound (pale yellow solid) using 26 mg (1.25 ml, 0.63 mmol) of LiOH (0.5 M aqueous solution).

PMR (acetone-d$_6$): δ1.29 (6H, s), 1.33 (9H, s), 2.34 (2H, d, J=4.8 Hz), 6.33 (1H, t, J=4.8 Hz), 7.45 (1H, dd, J=1.6, 7.9 Hz), 7.52 (1H, d, J=1.6 Hz), 7.64 (1H, d, J=8.1 Hz), 7.67 (2H, d, J=8.0 Hz), 8.06 (2H, d, J=8.0 Hz).

4-[(7,8-dihydro-5,8,8-trimethylnaphth-2-yl)ethynyl] benzoic acid (Compound 102)

Employing the same general procedure as for the preparation of 4-[(7,8-dihydro-8,8-dimethyl-5-phenylnaphth-2-yl)ethynyl]benzoic acid (Compound 97), 37 mg (0.11 mmol) of ethyl 4-[(7,8-dihydro-5,8,8-trimethylnaphth-2-yl) ethynyl]benzoate (Compound 95) was converted to the title compound (white solid) using 23 mg (1.1 ml, 0.54 mmol) of LiOH (0.5 M aqueous solution).

PMR (DMSO-d$_6$): δ1.21 (6H, s), 2.02 (3H, br s), 2.17 (2H, br s), 5.87 (1H, br s), 7.26 (1H, d, J=8.2 Hz), 7.40 (1H, d, J=8.2), 7.47 (1H, s), 7.65 (2H, d, J=8.1 Hz), 7.67 (2H, d, J=8.1 Hz).

4-[(7,8-dihydro-8,8-dimethyl-5-(1,1-dimethylethyl) naphth-2-yl)ethynyl]benzoic acid (Compound 103)

Employing the same general procedure as for the preparation of 4-[(7,8-dihydro-8,8-dimethyl-5-phenylnaphth-2-yl)ethynyl]benzoic acid (Compound 97), 51 mg (0.13 mmol) of ethyl 4-[(7,8-dihydro-8,8-dimethyl-5-(1,1-dimethylethyl)naphth-2-yl)ethynyl]benzoate (Compound 96) was converted to the title compound (white solid) using 28 mg (1.3 ml, 0.66 mmol) of LiOH (0.5 M aqueous solution).

PMR (acetone-d$_6$): δ1.24 (6H, s), 1.35 (9H, 5), 2.16 (2H, d, J=4.9 Hz), 6.06 (1H, t, J=4.9 Hz), 7.40 (1H, dd, J=2.0, 8.1

Hz), 7.50 (1H, d, J=2.0 Hz), 7.64 (2H, d, J=8.2 Hz), 7.71 (1H, d, J=8.1 Hz), 8.03 (2H, d, J=8.2 Hz).

4-[(7,8-dihydro-8,8-dimethyl-5-(2-thiazolyl)naphth-2-yl)ethynyl]benzoic acid (Compound 104)

Employing the same general procedure as for the preparation of 4-[(7,8-dihydro-8,8-dimethyl-5-phenylnaphth-2-yl)ethynyl]benzoic acid (Compound 97), 177 mg (0.43 mmol) of ethyl 4-[(7,8-dihydro-8,8-dimethyl-5-(2-thiazolyl) naphth-2-yl)ethynyl]benzoate (Compound 88) was converted to the title compound (white solid) using 91 mg (4.3 ml, 2.14 mmol) of LiOH (0.5M aqueous solution).

PMR (acetone-$d_6$): δ1.34 (6H, s), 2.45 (2H, d, J=4.9 Hz), 6.61 (1H, t, J=4.9 Hz), 7.42 (1H, dd, J=1.7, 8.1 Hz), 7.61 (2H, d, J=3.4 Hz), 7.67 (2H, d, J=8.2 Hz), 7.87 (1H, d, J=8.1 Hz), 7.92 (1H, d, J=1.7 Hz), 8.02 (2H, d, J=8.2 Hz).

Ethyl 4-[(5-cyano-5,6,7,8-tetrahydro-8,8-dimethyl-5-trimethylsiloxynaphth-2-yl)ethynyl]benzoate (Compound 107)

To 500 mg (1.28 mmol) of ethyl 4-[(5,6,7,8-tetrahydro-8,8-dimethyl-5-oxonaphth-2-yl)ethynyl]benzoate (Compound 1) was added 0.21 ml (1.40 mmol) of cyanotrimethylsilane and 6 drops of boron trifluoride etherate. The resulting dark mixture was heated at 60° C. for 30 minutes, cooled to room temperature and purified by flash chromatography (silica, 25% EtOAc-hexane) to yield the title compound as a clear oil.

PMR (CDCl$_3$): δ0.25 (9H, s), 1.34 (6H, s), 1.41 (3H, t, J=7.1 Hz), 1.90 (2H, m), 2.25 (1H, m), 2.35 (1H, m), 4.39 (2H, q, J=7.1 Hz), 7.44 (1H, dd, J=1.6, 8.4 Hz), 7.51 (1H, s), 7.61 (2H, d, J=8.4 Hz), 7.64 (1H, d, J=8.4 Hz), 8.04 (2H, d, J=8.3 Hz).

Ethyl 4-[(5-cyano-7,8-dihydro-8,8-dimethylnaphth-2-yl)ethynyl]benzoate (Compound 108)

To 215 mg (0.48 mmol) of ethyl 4-[(5-cyano-5,6,7,8-tetrahydro-8,8-dimethyl-5-trimethylsiloxynaphth-2-yl) ethynyl]benzoate (Compound 107) was added 0.5 ml of pyridine and 3 drops of phosphorous oxychloride. The resulting dark mixture was gently refluxed at 115° C. for 30 minutes, cooled to room temperature and poured into crushed ice. The mixture was extracted with Et$_2$O and the combined organic layers were washed with water, dilute HCl and water. The organic phase was concentrated in vacuo to a gummy residue which was purified by flash chromatography (silica, 20% EtOAc-hexane) to yield the title compound as a pale yellow solid.

PMR (CDCl$_3$): δ1.31 (6H, s), 1.41 (3H, t, J=7.2 Hz), 2.44 (2H, d, J=4.8 Hz), 4.39 (2H, q, J=7.2 Hz), 6.89 (1H, t, J=4.8 Hz), 7.49 (3H, m), 7.60 (2H, d, J=8.4 Hz), 8.03 (2H, d, J=8.4 Hz).

Ethyl 4-[(5-carboxamido-7,8-dihydro-8,8-dimethylnaphth-2-yl)ethynyl]benzoate (Compound 109)

To a solution of 50 mg (0.14 mmol) of ethyl 4-[(5-cyano-7,8-dihydro-8,8-dimethylnaphth-2-yl)ethynyl]benzoate (Compound 108) in 1 ml of ethanol was added 1 ml of H$_2$SO$_4$ (1M aqueous solution). This reaction mixture was heated at 80° C. overnight, 2 ml of water was added and the solution was extracted with EtOAc (3×2 ml). The combined organic layers were washed with sat. aqueous NaHCO$_3$ and brine, dried over MgSO$_4$, concentrated in vacuo and the residue purified by column chromatography (silica, 20% EtOAc-hexane) to yield the title compound as a colorless oil.

PMR (CDCl$_3$): δ1.31 (6H, s), 1.38 (3H, t, J=7.2 Hz), 2.46 (2H, d, J=4.8 Hz), 4.33–4.38 (4H, m), 6.98 (1H, t, J=4.8 Hz), 7.35 (2H, d, J=8.2 Hz), 7.56–7.59 (1H, d, J=8.0 Hz), 7.91 (1H, d, J=8.0 Hz), 7.97 (1H, s), 8.02 (2H, d, J=8.2 Hz).

Ethyl 4-[(7,8-dihydro-8,8-dimethylnaphth-2-yl) ethynyl]benzoate (Compound 110)

To a solution of 0.13 g (0.38 mmol) of ethyl 4-[(5,6,7,8-tetrahydro-5-hydroxy-8,8-dimethylnaphth-2-yl)ethynyl] benzoate (Compound 9) in 15 ml of dry benzene was added 0.67 g (2.90 mmol) of (methoxycarbonylsulfamoyl) triethylammonium hydroxide (Burgess Reagent). The resulting mixture was heated at 50° C. for 30 minutes, cooled to room temperature, partitioned between water (10 ml) and EtOAc (20 ml) and the layers separated. The organic layer was dried over Na$_2$SO$_4$, concentrated in vacuo and purified by flash chromatography (silica, 10% EtOAc-hexane) to yield the title compound as a clear oil.

PMR (CDCl$_3$): δ1.28 (6H, s), 1.40 (3H, t, J=7.1 Hz), 2.25 (2H, dd, J=1.8, 2.6 Hz), 4.37 (2H, g, J=7.1 Hz), 5.99 (1H, q, J=4.8 Hz), 6.45 (1H, d, J=9.7 Hz), 7.00 (1H, d, J=7.8 Hz), 7.32 (1H, dd, J=1.6 6.2 Hz), 7.46 (1H, s), 7.57 (2H, d, J=8.3 Hz), 8.02 (2H, d, J=8.5 Hz).

Ethyl 4-[(5,6,7,8-tetrahydro-5-hydroxy-8,8-dimethyl-5-carboethoxymethylnaphth-2-yl)ethynyl] benzoate (Compound 113)

To a refluxing solution of 1.00 g (15.30 mmol) of 20 mesh, granular zinc (activated prior to use by washing with 2% HCl, water, 95% ethanol, acetone, anhydrous Et$_2$O and then dried in vacuum for several hours) in 20 ml of dry benzene was slowly added a mixture of 0.23 ml (1.62 mmol) of ethyl bromoacetate, 0.28 g (0.81 mmol) of ethyl 4-[(5,6,7,8-tetrahydro-8,8-dimethyl-5-oxonaphth-2-yl)ethynyl] benzoate (Compound 1) in 10 ml of dry benzene. The resulting mixture was refluxed for 2 hours, cooled to room temperature and the precipitate filtered through Celite. The filtrate was washed with cold 15% H$_2$SO$_4$, sat. aqueous NaHCO$_3$ and brine. The organic phase was dried over Na$_2$SO$_4$ and concentrated in vacuo to a yellow oil. Purification by flash chromatography (silica, 10% EtOAc-hexane) yielded the title compound as a light yellow solid.

PMR (CDCl$_3$): δ1.30 (6H, s), 1.42 (3H, t, J=7.1 Hz), 1.75 (2H, m), 2.08 (2H, m), 2.77 (2H, s), 4.22 (3H, m), 4.39 (2H, q, J=7.1 Hz), 7.38 (1H, dd, J=1.7, 6.5 Hz), 7.49 (1H, d, J=1.6 Hz), 7.59 (3H, m), 8.02 (2H, d, J=8.4 Hz).

Ethyl 4-[(7,8-dihydro-8,8-dimethyl-5-carboethoxymethylnaphth-2-yl)ethynyl]benzoate (Compound 114) and Ethyl 4-[(5-carboethoxymethylidene-7,8-dihydro-8,8-dimethylnaphth-2-yl)ethynyl]benzoate (Compound 115)

To a solution of 0.50 g (1.15 mmol) of ethyl 4-[(7,8-dihydro-5-hydroxy-8,8-dimethyl-5-carboethoxymethylnaphth-2-yl)ethynyl]benzoate (Compound 113) in 25 ml of dry benzene was added 2.12 g (8.90 mmol) of (methoxycarbonylsulfamoyl) triethylammonium hydroxide (Burgess Reagent). The reaction mixture was heated at 50° C. for 30 minutes, cooled to room temperature and concentrated in vacuo. The residue was diluted with EtOAc, washed with water and brine, dried over Na$_2$SO$_4$ and concentrated in vacuo to an oil. Purification by flash chromatography (silica, 25% EtOAc-hexane) yielded the title compounds as solids in a ratio of 5 to 1, respectively.

Ethyl 4-[(7,8-dihydro-8,8-dimethyl-5-carboethoxymethylnaphth-2-yl)ethynyl]benzoate (Compound 114)

PMR (CDCl$_3$): δ1.17 (3H, t, J=2.8 Hz), 1.30 (6H, s), 1.41 (3H, t, J=7.1 Hz), 2.26 (2H, d, J=4.6 Hz), 3.46 (2H, s), 4.12

(2H, q, J=7.2 Hz), 4.38 (2H, q, J=7.1 Hz), 5.96 (1H, s), 7.17 (1H, d, J=8.0 Hz), 7.36 (1H, dd, J=1.7, 6.4 Hz), 7.48 (1H, d, J=1.7 Hz), 7.58 (2H, d, J=6.5 Hz), 8.01 (2H, d, J=6.5 Hz).

Ethyl 4-[(5-carboethoxymethylidene-7,8-dihydro-8,8-dimethylnaphth-2-yl)ethynyl]benzoate (Compound 115)

PMR (CDCl$_3$): δ1.32 (6H, s), 1.41 (3H, t, J=7.1 Hz), 1.73 (3H, t, J=6.7 Hz), 3.22 (2H, m), 4.22 (2H, q, J=7.1 Hz), 4.39 (2H, q, J=7.1 Hz), 6.30 (1H, d, J=1.8 Hz), 7.35 (1H, dd, J=1.7, 6.6 Hz), 7.55 (1H, d, J=1.6 Hz), 7.60 (3H, dd, J=2.0, 6.4 Hz), 8.04 (2H, d, J=6.5 Hz).

Trimethylsilylethyl 4-[(5,6,7,8-tetrahydro-8,8-dimethyl-5-oxonaphth-2-yl)ethynyl]benzoate (Compound 116)

To a solution of 0.24 g (0.73 mmol) of 4-[(5,6,7,8-tetrahydro-8,8-dimethyl-5-oxonaphth-2-yl)ethynyl]benzoic acid (Compound 7) in 10 ml of dry CH$_2$Cl$_2$ was added 0.09 g (0.74 mmol) of dimethylaminopyridine, 0.115 ml (0.80 mmol) of trimethylsilylethanol and 0.17 g (0.88 mmol) of 1-(3-dimethylaminopropyl)-3-ethyl carbodiimide hydrochloride. The reaction mixture was stirred at 25° C. for 5 hours, washed with sat. aqueous NaHCO$_3$ and brine, dried over Na$_2$SO$_4$ and concentrated in vacuo to an oil. Purification by flash chromatography (silica, 10% EtOAc-hexane) yielded the title compound as a white solid.

PMR (CDCl$_3$): δ0.09 (9H, s), 1.14 (2H, m), 1.42 (6H, s), 2.03 (2H, t, J=7.1 Hz), 2.74 (2H, t, J=6.5 Hz), 4.43 (2H, t, J=8.5 Hz), 7.45 (1H, dd, J=1.5, 6.7 Hz), 7.61 (3H, d, J=7.0 Hz), 8.03 (3H, t, J=6.7 Hz).

Trimethylsilylethyl 4-[(5,6,7,8-tetrahydro-5-hydroxy-8,8-dimethyl-5-carboethoxymethylnaphth-2-yl)ethynyl]benzoate (Compound 117)

Employing the same general procedure as for the preparation of ethyl 4-[(5,6,7,8-tetrahydro-5-hydroxy-8,8-dimethyl-5-carboethoxymethylnaphth-2-yl)ethynyl]benzoate (Compound 113), 0.38 g (0.89 mmol) of trimethylsilylethyl 4-[(5,6,7,8-tetrahydro-8,8-dimethyl-5-oxonaphth-2-yl)ethynyl]benzoate (Compound 116), was converted into the title compound (yellow solid) using 0.50 g (7.65 mmol) of zinc, 0.20 ml (1.78 mmol) of ethyl bromoacetate and 20 ml of dry benzene.

PMR (CDCl$_3$): δ0.09 (9H, s), 1.14 (2H, m), 1.28 (8H, m), 1.74 (2H, m), 2.07 (2H, m), 2.77 (2H, s), 4.20 (3H, m), 4.42 (3H, t, J=8.4 Hz), 7.37 (1H, dd, J=1.6, 6.7 Hz), 7.49 (1H, s), 7.58 (3H, dd, J=3.8, 7.0 Hz), 8.01 (2H, d, J=8.4 Hz).

4-[(5,6,7,8-tetrahydro-5-hydroxy-8,8-dimethyl-5-carboethoxymethylnaphth-2-yl)ethynyl]benzoic acid (Compound 118)

To a solution of 0.25 g (0.49 mmol) of trimethylsilylethyl 4-[(5,6,7,8-tetrahydro-5-hydroxy-8,8-dimethyl-5-carboethoxy-methylnaphth-2-yl)ethynyl]benzoate (Compound 117) in 5 ml of dry THF (flushed with argon) was added 1.48 ml (1.5 mmol) of tetrabutylammonium fluoride (1M solution in THF). The reaction mixture was stirred at room temperature for 12 hours, concentrated in vacuo to an oil and slowly diluted with water. The solution was acidified to pH 4 with 10% HCl and extracted with Et$_2$O. The organic layer was dried over Na$_2$SO$_4$, concentrated in vacuo to an oil and purified by flash chromatography (silica, 90% EtOAc-hexane) to give the title compound as a white solid.

PMR (CDCl$_3$): δ1.30 (9H, m), 1.72 (2H, m), 2.08 (2H, m), 2.78 (2H, s), 4.21 (2H, q, J=7.0 Hz), 7.38 (1H, dd, J=1.5, 6.6 Hz), 7.50 (1H, s), 7.58 (1H, d, J=8.2 Hz), 7.62 (2H, d, J=8.4 Hz), 8.10 (2H, d, J=8.4 Hz).

Ethyl 4-[(5-hydroxy-8,8-dimethyl-5-carboethoxymethyl-5,6,7,8-tetrahydronaphth-3-yl)ethynyl]benzoate (Compound 119)

Employing the same general procedure as for the preparation of ethyl 4-[(7,8-dihydro-5-hydroxy-8,8-dimethyl-5-carboethoxymethylnaphth-2-yl)ethynyl]benzoate (Compound 113), 1.00 g (2.88 mmol) of ethyl 4-[(5,6,7,8-tetrahydro-8,8-dimethyl-5-oxonaphth-3-yl)ethynyl]benzoate (Compound 2) was converted into the title compound (light yellow solid) using 1.00 g (15.30 mmol) of zinc, 0.639 ml (5.76 mmol) of ethyl bromoacetate and 70 ml of dry benzene.

PMR (CDCl$_3$): δ1.30 (9H, m), 1.40 (3H, t, J=7.1 Hz), 1.75 (2H, m), 2.04 (2H, m), 2.80 (2H, d, J=3.1 Hz), 4.21 (2H, m), 4.38 (2H, q, J=7.2 Hz), 7.30 (1H, d, J=8.3 Hz), 7.41 (1H, dd, J=1.8, 6.4 Hz), 7.57 (2H, d, J=6.7 Hz), 7.81 (1H, d, J=1.8 Hz), 8.03 (2H, d, J=8.4 Hz).

Ethyl 4-[(7,8-dihydro-8,8-dimethyl-5-carboethoxymethylnaphth-3-yl)ethynyl]benzoate (Compound 120) and Ethyl 4-[(5-carboethoxymethylidene-7,8-dihydro-8,8-dimethylnaphth-3-yl)ethynyl]benzoate (Compound 121)

Employing the same general procedure as for the preparations of ethyl 4-[(7,8-dihydro-8,8-dimethyl-5-carboethoxymethylnaphth-2-yl)ethynyl]benzoate (Compound 114) and ethyl 4-[(5-carboethoxymethylidene-7,8-dihydro-8,8-dimethylnaphth-2-yl)ethynyl]benzoate (Compound 115), 0.57 g (1.31 mmol) of ethyl 4-[(5,6,7,8-tetrahydro-5-hydroxy-8,8-dimethyl-5-carboethoxymethylnaphth-3-yl)ethynyl]benzoate (Compound 119) was converted into the title compounds (yellow solid and white solid, respectively) using 15 ml of dry benzene, 6 ml of dry THF and 2.42 g (10.1 mmol) of (methoxycarbonylsulfamoyl) triethylammonium hydroxide (Burgess Reagent).

Ethyl 4-[(7,8-dihydro-8,8-dimethyl-5-carboethoxymethylnaphth-3-yl)ethynyl]benzoate (Compound 120)

PMR (CDCl$_3$): δ1.22 (3H, t, J=7.1 Hz), 1.29 (6H, s), 2.70 (2H, d, J=4.4 Hz), 3.49 (2H, s), 4.17 (2H, q, J=7.1 Hz), 4.00 (2H, q, J=7.1 Hz), 5.96 (1H, t, J=4.5 Hz), 7.35 (3H, m), 7.58 (2H, d, J=8.4 Hz), 8.02 (2H, d, J=7.9 Hz).

Ethyl 4-[(5-carboethoxymethylidene-7,8-dihydro-8,8-dimethylnaphth-3-yl)ethynyl]benzoate (Compound 121)

PMR (CDCl$_3$): δ1.31 (9H, m), 1.74 (2H, q, J=6.7 Hz), 3.24 (2H, t, J=3.3 Hz), 4.22 (2H, q, J=7.1 Hz), 4.40 (2H, q, J=7.1 Hz), 6.33 (1H, s), 7.37 (1H, d, J=7.9 Hz), 7.50 (1H, d, J=8.3 Hz), 7.59 (2H, d, J=7.7 Hz), 7.79 (1H, s), 8.04 (2H, d, J=8.4 Hz).

Ethyl 4-[(7,8-dihydro-8,8-dimethyl-5-(2-furyl]naphth-3-yl)ethynyl]benzoate (Compound 122)

Employing the same general procedure as for the preparation of ethyl 4-[(7,8-dihydro-8,8-dimethyl-5-(2-thiazolyl)naphth-3-yl)ethynyl]benzoate (Compound 67), 250.0 mg (0.52 mmol) of ethyl 4-[(5-trifluoromethylsulfonyloxy-7,8-dihydro-8,8-dimethylnaphth-3-yl)ethynyl]benzoate (Compound 66) was converted into the title compound (colorless solid) using 142.4 mg (1.045 mmol) of zinc chloride, 24.1 mg (0.02 mmol) of tetrakis (triphenylphosphine)palladium(0) and 2-lithiofuran (prepared by the addition of 53.4 mg (0.52 ml, 0.78 mmol) of n-butyllithium (1.5M solution in hexane) to a cold solution (−78° C.) of 53.4 mg (0.784 mmol) of furan in 1.0 mL of THF).

PMR (CDCl$_3$): δ1.32 (6H, s), 1.41 (3H, t, J=7.1 Hz), 2.35 (2H, d, J=5.0 Hz), 4.39 (2H, q, J=7.1 Hz), 6.41 (1H, t, J=5.0 Hz), 6.50 (2H, s), 7.36 (1H, d, J=8.0 Hz), 7.45 (1H, dd, J=1.7, 8.0 Hz), 7.49 (1H, s), 7.57 (2H, d, J=8.2 Hz), 7.63 (1H, d, J=1.7 Hz), 8.02 (2H, d, J=8.2 Hz).

Ethyl 4-[(7,8-dihydro-8,8-dimethyl-5-(2-thienyl) naphth-3-yl)ethynyl]benzoate (Compound 123)

Employing the same general procedure as for the preparation of ethyl 4-[(7,8-dihydro-8,8-dimethyl-5-(2-thiazolyl) naphth-3-yl)ethynyl]benzoate (Compound 67), 328.0 mg (0.685 mmol) of ethyl 4-[(5-trifluoromethylsulfonyloxy-7,8-dihydro-8,8-dimethylnaphth-3-yl)ethynyl]benzoate (Compound 66) was converted into the title compound (colorless solid) using 186.8 mg (1.37 mmol) of zinc chloride 37.1 mg (0.03 mmol) of tetrakis(triphenylphosphine) palladium(0) and 2-lithiothiophene (prepared by the addition of 65.9 mg (0.69 ml, 1.03 mmol) of n-butyllithium (1.5M solution in hexane) to a cold solution (−78° C.) of 86.5 mg (1.03 mmol) of thiophene in 1.0 mL of THF).

PMR (CDCl$_3$): δ1.33 (6H, s), 1.36 (3H, t, J=7.1 Hz), 2.38 (2H, d, J=4.7 Hz), 4.34 (2H, q, J=7.2 Hz), 6.25 (1H, t, J=4.7 Hz), 7.13 (2H, m), 7.47 (4H, m), 7.62 (2H, d, J=8.5 Hz), 8.00 (2H, d, J=8.5 Hz).

4-[(7,8-dihydro-8,8-dimethyl-5-(2-furyl)naphth-3-yl) ethynyl]benzoic acid (Compound 124)

Employing the same general procedure as for the preparation of 4-[(7,8-dihydro-8,8-dimethyl-5-(1-pentynyl) naphth-3-yl)ethynyl]benzoic acid (Compound 84), 60.3 mg (0.15 mmol) of ethyl 4-[(7,8-dihydro-8,8-dimethyl-5-(2-furyl)naphth-3-yl)ethynyl]benzoate (Compound 122) was converted into the title compound (colorless solid) using 16.0 mg (0.38 mmol) of LiOH in H$_2$O.

PMR (d$_6$-DMSO): δ1.26 (6H, s), 2.33 (2H, d, J=4.9 Hz), 6.41 (1H, t, J=4.9 Hz), 6.60 (2H, m), 7.45–7.53 (3H, m), 7.64 (2H, d, J=8.3 Hz), 7.75 (1H, d, J=1.6 Hz), 7.93 (2H, d, J=8.3 Hz).

4-[(7,8-dihydro-8,8-dimethyl-5-(2-thienyl)naphth-3-yl)ethynyl]benzoic acid (Compound 125)

Employing the same general procedure as for the preparation of 4-[(7,8-dihydro-8,8-dimethyl-5-(1-pentynyl) naphth-2-yl)ethynyl]benzoic acid (Compound 84), 70.0 mg (0.17 mmol) of ethyl 4-[(7,8-dihydro-8,8-dimethyl-5-(2-thienyl)naphth-3-yl)ethynyl]benzoate (Compound 123) was converted into the title compound (colorless solid) using 17.8 mg (0.42 mmol) of LiOH in H$_2$O.

PMR (d$_6$-DMSO): δ1.27 (6H, s), 2.33 (2H, d, J=4.9 Hz), 6.23 (1H, t, J=4.9 Hz), 7.14 (2H, m), 7.38– 7.56 (4H, m), 7.61 (2H, d, J=8.3 Hz), 7.92 (2H, d, J=8.3 Hz).

4-[(5-cyano-7,8-dihydro-8,8-dimethylnaphth-3-yl) ethynyl]benzoic acid (Compound 129)

To 76 mg (0.24 mmol) of 4-[(5,6,7,8-tetrahydro-8,8-dimethyl-5-oxonaphth-3-yl)ethynyl]benzoic acid (Compound 8) was added 0.06 ml (0.48 mmol) of cyanotrimethylsilane and 6 drops of boron trifluoride etherate. The resulting dark mixture was heated at 80° C. for 45 minutes, cooled to room temperature and purified by flash chromatography (silica, 50% EtOAc-hexane) to yield the title compound as a yellow solid.

PMR (CDCl$_3$): δ1.31 (6H, s), 2.45 (2H, d, J=4.8 Hz), 6.91 (1H, t, J=4.8 Hz), 7.36 (1H, d, J=8.0 Hz), 7.51 (1H, dd, J=1.8, 8.0 Hz), 7.65 (2H, d, J=8.4 Hz), 7.69 (1H, s), 8.10 (2H, d, J=8.4 Hz).

4-[(5-cyano-7,8-dihydro-8 8-dimethylnaphth-2-yl) ethynyl]benzoic acid (Compound 130)

Employing the same general procedure as for the preparation of 4-[(8-cyano-7,8-dihydro-8,8-dimethylnaphth-3-yl) ethynyl]benzoic acid (Compound 129), 63 mg (0.26 mmol) of 4-[(5,6,7,8-tetrahydro-8,8-dimethyl-5-oxonaphth-2-yl) ethynyl]benzoic acid (Compound 7) was converted into the title compound (yellow powder) using 0.06 ml (0.54 mmol) of cyanotrimethylsilane and 6 drops of boron trifluoride etherate.

PMR (CDCl$_3$): δ1.32 (6H, s), 2.45 (2H, d, J=4.8 Hz), 6.90 (1H, t, J=4.8 Hz), 7.49 (3H, m), 7.65 (2H, d, J=8.4 Hz), 8.10 (2H, d, J=8.4 Hz).

Ethyl 4-[(7,8-dihydro-8,8-dimethyl-5-(4-methylphenyl)naphth-3-yl)ethynyl]benzoate (Compound 163)

Employing the same general procedure as for the preparation of ethyl 4-[(7,8-dihydro-8,8-dimethyl-5-(2-thiazolyl) naphth-3-yl)ethynyl]benzoate (Compound 67), 200.0 mg (0.42 mmol) of ethyl 4-[(5-triflouromethylsulfonyloxy-7,8-dihydro-8,8-dimethylnaphth-3-yl)ethynyl]benzoate (Compound 66) was converted into the title compound (colorless solid) using 113.8 mg (0.835 mmol) of zinc chloride and 4-methylphenyllithium (prepared by adding 40.4 mg (0.42 ml, 0.63 mmol) of n-butyllithium (1.5 M solution in hexane) to a cold solution (−78° C.) of 108.0 mg (0.63 mmol) of 4-bromotoluene in 1.0 ml of THF).

PMR (CDCl$_3$): δ1.36 (6H, s), 1.41 (3H, t, J=7.2 Hz), 2.36 (2H, d, J=4.7 Hz), 2.43 (3H, s), 4.39 (2H, q, J=7.2 Hz), 6.01 (1H, t, J=4.7 Hz), 7.26 (4H, m), 7.40 (2H, m ), 7.53 (2H, d, J=8.4 Hz), 7.90 (2H, d, J=8.4 Hz).

4-[(7,8-dihydro-8,8-dimethyl-5-(4-methylphenyl) naphth-2-yl)ethynyl]benzoic acid (Compound 164)

Employing the same general procedure as for the preparation of 4-[(7,8-dihydro-8,8-dimethyl-5-(2-thiazolyl) naphth-3-yl)ethynyl]benzoic acid (Compound 78), 26.0 mg (0.06 mmol) of ethyl 4-[(7,8-dihydro-8,8-dimethyl-5-(4-methylphenyl)naphth-3-yl)ethynyl]benzoate (Compound 163) was converted into the title compound (colorless solid) using 6.5 mg (0.16 mmol) of LiOH in H$_2$O.

PMR (d$_6$-DMSO): δ1.28 (6H, s), 2.31 (2H, d, J=4.7 Hz), 2.33 (3H, s) 5.98 (1H, t, J=4.5 Hz), 7.00 (1H, s), 7.20 (4H, m), 7.44 (2H, d, J=8.5 Hz), 7.58 (2H, d, J=8.5 Hz), 7.90 (2H, d, J=8.3 Hz).

What is claimed is:

1. A compound of the formula

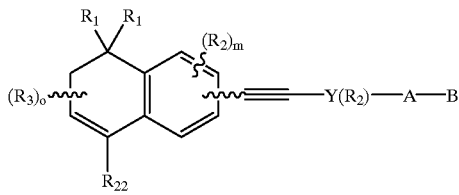

wherein $R_1$ is hydrogen or alkyl of 1 to 10 carbons;

$R_2$ and $R_3$ are hydrogen, or alkyl of 1 to 6 carbons and the substituted ethynyl group occupies either the 2 or the 3 position of the dihydronaphthalene nucleus;

m is an integer having the value of 0–3;

o is an integer having the value 0–3;

Y is heteroaryl selected from a group consisting of pyridyl, thienyl, furyl, pyridazinyl, pyrimidinyl, pyrazinyl, thiazolyl, oxazolyl, and imidazolyl, said groups being optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{22}$ is hydrogen, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, hydroxy alkyl of 1 to 10 carbons, hydroxyalkynyl having 2 to 10 carbons and 1 to 3 triple bonds, acyloxyalkyl of 1 to 10 carbons or acyloxyalkynyl of 2 to 10 carbons and 1 to 3 triple bonds where the acyl group is represented by $COR_{14}$, CN, $CON(R_1)_2$, $(CH_2)_pCO_2R_8$ where p is an integer between 0 to 10, or $R_{22}$ is aminoalkyl or thioalkyl of 1 to 10 carbons, or $R_{22}$ is represented by $(CH_2)_pXR_1$ or by $(CH_2)_pNR_1R_2$; where X is O or S, the $R_{14}$ group is hydrogen, alkyl of 1 to 10 carbons, alkenyl of 2 to 10 carbons and having 1 to 3 double bond, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, or naphthyl-$C_1$–$C_{10}$alkyl.

2. A compound of claim 1 where Y is pyridyl, thienyl or furyl.

3. A compound of claim 1 where Y is pyridyl.

4. A compound of claim 3 where the pyridyl ring is substituted in the 2 and 5 positions.

5. A compound of claim 1 where Y is thienyl or furyl.

6. A compound of claim 1 where $R_2$ is hydrogen.

7. A compound of claim 1 where $R_3$ is hydrogen.

8. A compound of claim 1 where $R_{22}$ is hydrogen, alkyl of 1–10 carbons, alkynyl of 2 to 10 carbons having 1 triple bond, $CH_2CO_2R_8$, hydroxyalkyl having 1 to 10 carbons in the alkyl group or hydroxyalkynyl having 2 to 10 carbons in the alkynyl group.

9. A compound of claim 1 where $R_{22}$ is cyano (CN) or $CONH_2$.

10. A compound of the formula

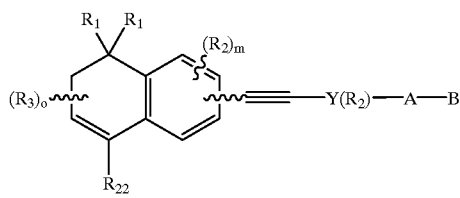

wherein $R_1$ is hydrogen or alkyl of 1 to 10 carbons;

$R_2$ and $R_3$ are hydrogen, or alkyl of 1 to 6 carbons and the substituted ethynyl group occupies either the 2 or the 3 position of the dihydronaphthalene nucleus;

m is an integer having the value of 0–3;

o is an integer having the value 0–3;

Y is pyridyl optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is a divalent alkyl radical 2–5 carbons, and $R_{22}$ is hydrogen, alkyl of 1 to 10 carbons, alkenyl of 2 to 10 carbons and having 1 to 3 double bonds, alkynyl having 2 to 10 carbons and 1 to 3 triple bonds, hydroxy alkyl of 1 to 10 carbons, hydroxyalkynyl having 2 to 10 carbons and 1 to 3 triple bonds, acyloxyalkyl of 1 to 10 carbons or acyloxyalkynyl of 2 to 10 carbons and 1 to 3 triple bonds where the acyl group is represented by $COR_{14}$, CN, $CON(R_1)_2$, $(CH_2)_pCO_2R_8$ where p is an integer between 0 to 10, where the $R_{14}$ group is hydrogen, alkyl of 1 to 10 carbons, alkenyl of 2 to 10 carbons and having 1 to 3 double bond, alkynyl having 2 to 10 carbons and 1 to 3 triple bonds, carbocyclic aryl selected from the group consisting of phenyl, $C_1$–$C_{10}$-alkylphenyl, or phenyl-$C_1$–$C_{10}$-alkyl.

11. A compound of claim 10 where A is $(CH_2)_n$ where n is 0–5 and where B is COOH or a pharmaceutically acceptable salt thereof, $COOR_8$, or $CONR_9R_{10}$.

12. A compound of claim 11 where n is 0 and B is COOH or a pharmaceutically acceptable salt thereof.

13. A compound of the formula

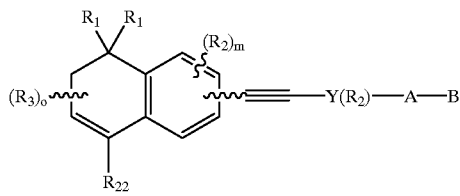

wherein

R₁ is hydrogen or alkyl of 1 to 10 carbons;

R₂ and R₃ are hydrogen, or alkyl of 1 to 6 carbons and the substituted ethynyl group occupies either the 2 or the 3 position of the dihydronaphthalene nucleus;

m is an integer having the value of 0–3;

o is an integer having the value 0–3;

Y is a pyridazinyl, pyrimidinyl, pyrazinyl, oxazolyl, and imidazolyl, said groups being optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{22}$ is hydrogen, alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, naphthyl-$C_1$–$C_{10}$alkyl, $C_1$–$C_{10}$-alkenylphenyl having 1 to 3 double bonds, $C_1$–$C_{10}$-alkynylphenyl having 1 to 3 triple bonds, phenyl-$C_1$–$C_{10}$alkenyl having 1 to 3 double bonds, phenyl-$C_1$–$C_{10}$alkynyl having 1 to 3 triple bonds, hydroxy alkyl of 1 to 10 carbons, hydroxyalkynyl having 2 to 10 carbons and 1 to 3 triple bonds, acyloxyalkyl of 1 to 10 carbons or acyloxyalkynyl of 2 to 10 carbons and 1 to 3 triple bonds where the acyl group is represented by $COR_{14}$, CN, $CON(R_1)_2$, $(CH_2)_pCO_2R_8$ where p is an integer between 0 to 10, or $R_{22}$ is aminoalkyl or thioalkyl of 1 to 10 carbons, or a 5 or 6 membered heteroaryl group optionally substituted with a $C_1$ to $C_{10}$ alkyl group and having 1 to 3 heteroatoms, said heteroatoms being selected from a group consisting of O, S, and N, or $R_{22}$ is represented by $(CH_2)_pXR_1$ or by $(CH_2)_pNR_1R_1R_2$; where X is O or S, the $R_{14}$ group is hydrogen, alkyl of 1 to 10 carbons, alkenyl of 2 to 10 carbons and having 1 to 3 double bond, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, or naphthyl-$C_1$–$C_{10}$alkyl.

* * * * *

UNITED STATES PATENT AND TRADEMARK OFFICE
CERTIFICATE OF CORRECTION

PATENT NO.    : 6,355,806 B1
DATED         : March 12, 2002
INVENTOR(S)   : Johnson et al.

It is certified that error appears in the above-identified patent and that said Letters Patent is hereby corrected as shown below:

<u>Title page,</u>
Item [56], OTHER PUBLICATIONS, "Viteoretinopathy" should be
-- Vitreoretinopathy --.

<u>Column 2,</u>
Line 41, insert -- 7 -- after "compounds of Formula".

<u>Column 3,</u>
Line 40, "$(CH_2)_pNR_{12}$" should be -- $(CH_2)_pNR_1R_2$ --.
Line 64, "In. addition" should be -- In addition --.

<u>Column 5,</u>
Line 16, "$-CH_2OCOR_1$," should be -- $-CH_2OCOR_{11}$ --.

<u>Column 11,</u>
Reaction scheme 1, formula 13 → formula 16, to the right of the arrow, "TMSCI" should be -- TMSCl --.

<u>Column 12,</u>
Line 48, "$Z_1-Y(R_2)-A-B'$" should be -- $X_1-Y(R_2)-A-B'$ --.

<u>Column 15,</u>
Line 8, "Formula IS" should be -- Formula I5 --.

<u>Column 18,</u>
Line 2, "(Compound B)" should be -- (Compound H) --.

<u>Column 19,</u>
Line 60, "$(Pd(PPh_3)4)$" should be -- $(Pd(PPh_3)_4)$ --.

<u>Column 24,</u>
Line 50, "(1H, 5)" should be -- (1H, s) --.
Line 63, both occurrences of "J-7" should be -- J~7 --.

<u>Column 25,</u>
Lines 6-7, all five occurrences of "J-" should be -- J~ --.

UNITED STATES PATENT AND TRADEMARK OFFICE
CERTIFICATE OF CORRECTION

PATENT NO. : 6,355,806 B1
DATED : March 12, 2002
INVENTOR(S) : Johnson et al.

It is certified that error appears in the above-identified patent and that said Letters Patent is hereby corrected as shown below:

Column 28,
Line 10, "ml(2" should be -- ml (2 --.

Column 31,
Line 7, "4-(7,8-dihydro" should be -- 4[(7,8-dihydro --.

Column 37,
Line 38, "(6H, S)" should be -- (6H, s) --.

Column 38,
Line 66, "(9H, 5)" should be -- (9H, s) --.

Column 40,
Line 19, "(2H, g" should be -- (2H, q --.
Line 21, "J=1.6 6.2 Hz" should be -- J = 1.6, 6.2 Hz --.

Column 48,
Line 30, "$(CH_2)_p NR_1 R_1 R_2$" should be -- $(CH_2)_p NR_1 R_2$ --.

Signed and Sealed this

Twenty-seventh Day of May, 2003

JAMES E. ROGAN
*Director of the United States Patent and Trademark Office*